United States Patent
Tonar et al.

(10) Patent No.: US 11,832,929 B2
(45) Date of Patent: *Dec. 5, 2023

(54) APPARATUS AND METHODS FOR DETERMINING DAMAGED TISSUE USING SUB-EPIDERMAL MOISTURE MEASUREMENTS

(71) Applicant: Bruin Biometrics, LLC, Los Angeles, CA (US)

(72) Inventors: Ya-Chen Tonar, San Pedro, CA (US); Shannon Rhodes, Venice, CA (US); Marta Clendenin, San Diego, CA (US); Martin F. Burns, Los Angeles, CA (US); Kindah Jaradeh, Sun Valley, CA (US)

(73) Assignee: Bruin Biometrics, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/346,114

(22) Filed: Jun. 30, 2023

(65) Prior Publication Data
US 2023/0346240 A1 Nov. 2, 2023

Related U.S. Application Data

(63) Continuation of application No. 17/700,888, filed on Mar. 22, 2022, which is a continuation of application
(Continued)

(51) Int. Cl.
*A61B 5/0537* (2021.01)
*A61B 5/00* (2006.01)
*A61B 5/0531* (2021.01)

(52) U.S. Cl.
CPC .......... *A61B 5/0537* (2013.01); *A61B 5/0531* (2013.01); *A61B 5/445* (2013.01);
(Continued)

(58) Field of Classification Search
CPC ..... A61B 5/0537; A61B 5/0531; A61B 5/445; A61B 5/447; A61B 5/4875; A61B 5/6801;
(Continued)

(56) References Cited

U.S. PATENT DOCUMENTS

| 3,851,641 A | 12/1974 | Toole et al. |
| 4,295,009 A | 10/1981 | Weidler |

(Continued)

FOREIGN PATENT DOCUMENTS

| AU | 2020103438 A4 | 1/2021 |
| CA | 2811609 | 11/2011 |

(Continued)

OTHER PUBLICATIONS

U.S. Appl. No. 18/064,446, filed Dec. 12, 2022, which is pending.
(Continued)

*Primary Examiner* — Patrick Fernandes
(74) *Attorney, Agent, or Firm* — Arnold & Porter Kaye Scholer LLP

(57) ABSTRACT

The present disclosure provides apparatuses and computer readable media for measuring sub-epidermal moisture in patients to determine damaged tissue for clinical intervention. The present disclosure also provides methods for determining damaged tissue.

30 Claims, 16 Drawing Sheets

Related U.S. Application Data

No. 16/440,743, filed on Jun. 13, 2019, now Pat. No. 11,284,810, which is a continuation of application No. 15/280,528, filed on Sep. 29, 2016, now Pat. No. 9,763,596, and a continuation of application No. 15/280,487, filed on Sep. 29, 2016, now Pat. No. 10,485,447, said application No. 15/280,528 is a continuation of application No. 15/273,202, filed on Sep. 22, 2016, now Pat. No. 10,178,961, said application No. 15/280,487 is a continuation of application No. 15/273,202, filed on Sep. 22, 2016, now Pat. No. 10,178,961, which is a continuation of application No. 15/134,110, filed on Apr. 20, 2016, now Pat. No. 10,182,740.

(60) Provisional application No. 62/152,549, filed on Apr. 24, 2015.

(52) U.S. Cl.
CPC ............ *A61B 5/447* (2013.01); *A61B 5/4875* (2013.01); *A61B 5/6801* (2013.01); *A61B 5/7278* (2013.01); *A61B 5/742* (2013.01); *A61B 5/746* (2013.01); *A61B 5/6843* (2013.01); *A61B 2560/0468* (2013.01); *A61B 2562/046* (2013.01)

(58) Field of Classification Search
CPC ....... A61B 5/7278; A61B 5/742; A61B 5/746; A61B 5/6843; A61B 2560/0468; A61B 2562/046; A61B 2562/0214; G16H 50/30; G16H 50/20; A61G 7/057
See application file for complete search history.

(56) References Cited

U.S. PATENT DOCUMENTS

| | | |
|---|---|---|
| 4,557,271 A | 12/1985 | Stoller et al. |
| 4,857,716 A | 8/1989 | Gombrich et al. |
| 4,860,753 A | 8/1989 | Amerena |
| 5,001,436 A | 3/1991 | Scot |
| 5,073,126 A | 12/1991 | Kikuchi et al. |
| 5,284,150 A | 2/1994 | Butterfield et al. |
| 5,292,341 A | 3/1994 | Snell |
| 5,367,789 A | 11/1994 | Lamont |
| 5,815,416 A | 9/1998 | Liebmann et al. |
| 5,904,581 A | 5/1999 | Pope et al. |
| 6,223,088 B1 | 4/2001 | Scharnberg et al. |
| 6,312,263 B1 | 11/2001 | Higuchi et al. |
| 6,330,479 B1 | 12/2001 | Stauffer |
| 6,368,284 B1 | 4/2002 | Bardy |
| 6,370,426 B1 | 4/2002 | Campbell et al. |
| 6,434,422 B1 | 8/2002 | Tomoda et al. |
| 6,577,700 B1 | 6/2003 | Fan et al. |
| 6,634,045 B1 | 10/2003 | DuDonis et al. |
| 6,738,798 B1 | 5/2004 | Ploetz et al. |
| 6,756,793 B2 | 6/2004 | Hirono et al. |
| 6,963,772 B2 | 11/2005 | Bloom et al. |
| 7,079,899 B2 | 7/2006 | Petrofsky |
| 7,315,767 B2 | 1/2008 | Caduff et al. |
| 7,402,135 B2 | 7/2008 | Leveque et al. |
| 7,783,344 B2 | 8/2010 | Lackey et al. |
| 8,011,041 B2 | 9/2011 | Hann |
| 8,060,315 B2 | 11/2011 | Brosette et al. |
| 8,355,925 B2 | 1/2013 | Rothman et al. |
| 8,390,583 B2 | 3/2013 | Forutanpour et al. |
| 8,494,617 B2 | 7/2013 | Baker, Jr. et al. |
| 8,648,707 B2 | 2/2014 | Franz et al. |
| 8,690,785 B2 | 4/2014 | Lading |
| 8,925,392 B2 | 1/2015 | Esposito et al. |
| 9,028,407 B1 | 5/2015 | Bennett-Guerrero |
| 9,095,305 B2 | 8/2015 | Engler et al. |
| 9,220,455 B2 | 12/2015 | Sarrafzadeh et al. |
| 9,271,676 B2 | 3/2016 | Alanen et al. |
| 9,398,879 B2 | 7/2016 | Sarrafzadeh et al. |
| 9,675,289 B2 | 6/2017 | Heaton |
| 9,763,596 B2 | 9/2017 | Tonar et al. |
| 9,949,683 B2 | 4/2018 | Afentakis |
| 9,980,673 B2 | 5/2018 | Sarrafzadeh et al. |
| 10,085,643 B2 | 10/2018 | Bandic et al. |
| 10,166,387 B2 | 1/2019 | Bergelin et al. |
| 10,178,961 B2 | 1/2019 | Tonar et al. |
| 10,182,740 B2 | 1/2019 | Tonar et al. |
| 10,188,340 B2 | 1/2019 | Sarrafzadeh et al. |
| 10,194,856 B2 | 2/2019 | Afentakis et al. |
| 10,206,604 B2 | 2/2019 | Bergelin et al. |
| 10,226,187 B2 | 3/2019 | Al-Ali et al. |
| 10,278,636 B2 | 5/2019 | Wu et al. |
| 10,285,898 B2 | 5/2019 | Douglas et al. |
| 10,307,060 B2 | 6/2019 | Tran |
| 10,342,482 B1 | 7/2019 | Lisy et al. |
| 10,383,527 B2 | 8/2019 | Al-Ali |
| 10,420,602 B2 | 9/2019 | Horton et al. |
| 10,441,185 B2 | 10/2019 | Rogers et al. |
| 10,448,844 B2 | 10/2019 | Al-Ali et al. |
| 10,463,293 B2 | 11/2019 | Maharbiz et al. |
| 10,485,447 B2 | 11/2019 | Tonar et al. |
| 10,898,129 B2 | 1/2021 | Burns et al. |
| 10,950,960 B2 | 3/2021 | Burns et al. |
| 11,191,477 B2 | 12/2021 | Burns |
| 11,253,192 B2 | 2/2022 | Sarrafzadeh et al. |
| 11,284,810 B2 | 3/2022 | Tonar et al. |
| 11,304,652 B2 | 4/2022 | Burns et al. |
| 11,337,651 B2 | 5/2022 | Burns et al. |
| 11,342,696 B2 | 5/2022 | Burns et al. |
| 11,426,118 B2 | 8/2022 | Burns |
| 11,534,077 B2 | 12/2022 | Tonar et al. |
| 2001/0051783 A1 | 12/2001 | Edwards et al. |
| 2002/0016535 A1 | 2/2002 | Martin et al. |
| 2002/0070866 A1 | 6/2002 | Newham |
| 2002/0112898 A1 | 8/2002 | Honda et al. |
| 2002/0143262 A1 | 10/2002 | Bardy |
| 2003/0009244 A1 | 1/2003 | Engleson et al. |
| 2003/0036674 A1 | 2/2003 | Bouton |
| 2003/0036713 A1 | 2/2003 | Bouton et al. |
| 2003/0110662 A1 | 6/2003 | Gilman et al. |
| 2003/0116447 A1 | 6/2003 | Surridge et al. |
| 2003/0139255 A1 | 7/2003 | Lina |
| 2004/0041029 A1 | 3/2004 | Postman et al. |
| 2004/0046668 A1 | 3/2004 | Smith et al. |
| 2004/0054298 A1 | 3/2004 | Masuo et al. |
| 2004/0080325 A1 | 4/2004 | Ogura |
| 2004/0133092 A1 | 7/2004 | Kain |
| 2004/0147977 A1 | 7/2004 | Petrofsky |
| 2004/0171962 A1 | 9/2004 | Leveque et al. |
| 2004/0176754 A1 | 9/2004 | Island et al. |
| 2004/0236200 A1 | 11/2004 | Say et al. |
| 2004/0254457 A1 | 12/2004 | Van der Weide |
| 2005/0027175 A1 | 2/2005 | Yang |
| 2005/0070778 A1 | 3/2005 | Lackey et al. |
| 2005/0086072 A1 | 4/2005 | Fox et al. |
| 2005/0096513 A1 | 5/2005 | Ozguz et al. |
| 2005/0177061 A1 | 8/2005 | Alanen et al. |
| 2005/0203435 A1 | 9/2005 | Nakada |
| 2005/0215918 A1 | 9/2005 | Frantz et al. |
| 2005/0245795 A1 | 11/2005 | Goode et al. |
| 2005/0251418 A1 | 11/2005 | Fox et al. |
| 2006/0052678 A1 | 3/2006 | Drinan et al. |
| 2006/0058593 A1 | 3/2006 | Drinan et al. |
| 2006/0097949 A1 | 5/2006 | Luebke et al. |
| 2006/0206013 A1 | 9/2006 | Rothman et al. |
| 2007/0043282 A1 | 2/2007 | Mannheimer et al. |
| 2007/0106172 A1 | 5/2007 | Abreu |
| 2007/0179585 A1 | 8/2007 | Chandler et al. |
| 2007/0191273 A1 | 8/2007 | Ambati et al. |
| 2007/0213700 A1 | 9/2007 | Davison et al. |
| 2007/0248542 A1 | 10/2007 | Kane et al. |
| 2008/0009764 A1 | 1/2008 | Davies |
| 2008/0015894 A1 | 1/2008 | Miller et al. |
| 2008/0039700 A1 | 2/2008 | Drinan et al. |
| 2008/0048680 A1 | 2/2008 | Hargreaves et al. |
| 2008/0259577 A1 | 10/2008 | Hu et al. |

(56) References Cited

U.S. PATENT DOCUMENTS

| | | |
|---|---|---|
| 2008/0278336 A1 | 11/2008 | Ortega et al. |
| 2009/0047694 A1 | 2/2009 | Shuber |
| 2009/0076410 A1 | 3/2009 | Libbus et al. |
| 2009/0104797 A1 | 4/2009 | Tseng et al. |
| 2009/0124924 A1 | 5/2009 | Eror et al. |
| 2009/0189092 A1 | 7/2009 | Aoi et al. |
| 2009/0209830 A1 | 8/2009 | Nagle et al. |
| 2009/0285785 A1 | 11/2009 | Jimi et al. |
| 2009/0326346 A1 | 12/2009 | Kracker et al. |
| 2010/0017182 A1 | 1/2010 | Voros et al. |
| 2010/0030167 A1 | 2/2010 | Thirstrup et al. |
| 2010/0042389 A1 | 2/2010 | Farruggia et al. |
| 2010/0073170 A1 | 3/2010 | Siejko et al. |
| 2010/0113979 A1 | 5/2010 | Sarrafzadeh et al. |
| 2010/0268111 A1 | 10/2010 | Drinan et al. |
| 2010/0298687 A1 | 11/2010 | Yoo et al. |
| 2010/0312233 A1 | 12/2010 | Furnish et al. |
| 2010/0324455 A1 | 12/2010 | Rangel et al. |
| 2010/0324611 A1 | 12/2010 | Deming et al. |
| 2011/0046505 A1 | 2/2011 | Cornish et al. |
| 2011/0160548 A1 | 6/2011 | Forster |
| 2011/0175844 A1 | 7/2011 | Berggren et al. |
| 2011/0184264 A1 | 7/2011 | Galasso et al. |
| 2011/0191122 A1 | 8/2011 | Kharraz Tavakol et al. |
| 2011/0237926 A1 | 9/2011 | Jensen |
| 2011/0263950 A1 | 10/2011 | Larson et al. |
| 2011/0301441 A1 | 12/2011 | Bandic et al. |
| 2011/0313311 A1 | 12/2011 | Gaw |
| 2012/0029410 A1 | 2/2012 | Koenig et al. |
| 2012/0061257 A1 | 3/2012 | Yu et al. |
| 2012/0078088 A1 | 3/2012 | Whitestone et al. |
| 2012/0150011 A1 | 6/2012 | Besio |
| 2012/0179006 A1 | 7/2012 | Jansen et al. |
| 2012/0190989 A1 | 7/2012 | Kaiser et al. |
| 2012/0271121 A1 | 10/2012 | Della Torre et al. |
| 2013/0041235 A1 | 2/2013 | Rogers et al. |
| 2013/0072870 A1 | 3/2013 | Heppe et al. |
| 2013/0121544 A1 | 5/2013 | Sarrafzadeh et al. |
| 2013/0123587 A1 | 5/2013 | Sarrafzadeh et al. |
| 2013/0137951 A1 | 5/2013 | Chuang et al. |
| 2013/0253285 A1 | 9/2013 | Bly et al. |
| 2013/0261496 A1 | 10/2013 | Engler et al. |
| 2013/0301255 A1 | 11/2013 | Kim et al. |
| 2013/0310440 A1 | 11/2013 | Duskin et al. |
| 2013/0333094 A1 | 12/2013 | Rogers et al. |
| 2013/0338661 A1 | 12/2013 | Behnke, II |
| 2014/0121479 A1 | 5/2014 | O'Connor et al. |
| 2014/0142984 A1 | 5/2014 | Wright et al. |
| 2014/0200486 A1 | 7/2014 | Bechtel et al. |
| 2014/0221792 A1 | 8/2014 | Miller et al. |
| 2014/0273025 A1 | 9/2014 | Hurskainen et al. |
| 2014/0275823 A1 | 9/2014 | Lane et al. |
| 2014/0288397 A1 | 9/2014 | Sarrafzadeh et al. |
| 2014/0298928 A1 | 10/2014 | Duesterhoft et al. |
| 2014/0316297 A1 | 10/2014 | McCaughan et al. |
| 2014/0318699 A1 | 10/2014 | Longinotti-Buitoni et al. |
| 2015/0002168 A1 | 1/2015 | Kao et al. |
| 2015/0009168 A1 | 1/2015 | Levesque et al. |
| 2015/0094548 A1 | 4/2015 | Sabatini et al. |
| 2015/0157435 A1 | 6/2015 | Chasins et al. |
| 2015/0186607 A1 | 7/2015 | Gileijnse et al. |
| 2015/0230863 A1 | 8/2015 | Youngquist et al. |
| 2015/0343173 A1 | 12/2015 | Tobescu et al. |
| 2015/0363567 A1 | 12/2015 | Pettus |
| 2015/0366499 A1 | 12/2015 | Sarrafzadeh et al. |
| 2015/0371522 A1 | 12/2015 | Mravyan et al. |
| 2016/0015962 A1 | 1/2016 | Shokoueinejad Maragheh et al. |
| 2016/0038055 A1 | 2/2016 | Wheeler et al. |
| 2016/0058342 A1 | 3/2016 | Maiz-Aguinaga et al. |
| 2016/0072308 A1 | 3/2016 | Nyberg et al. |
| 2016/0100790 A1 | 4/2016 | Cantu et al. |
| 2016/0101282 A1 | 4/2016 | Bergelin et al. |
| 2016/0174631 A1 | 6/2016 | Tong et al. |
| 2016/0174871 A1 | 6/2016 | Sarrafzadeh et al. |
| 2016/0220172 A1 | 8/2016 | Sarrafzadeh et al. |
| 2016/0270672 A1 | 9/2016 | Chen et al. |
| 2016/0270968 A1 | 9/2016 | Stanford et al. |
| 2016/0278692 A1 | 9/2016 | Larson et al. |
| 2016/0296268 A1 | 10/2016 | Gee et al. |
| 2016/0310034 A1 | 10/2016 | Tonar et al. |
| 2016/0338591 A1 | 11/2016 | Lachenbruch et al. |
| 2017/0007153 A1 | 1/2017 | Tonar et al. |
| 2017/0014044 A1 | 1/2017 | Tonar et al. |
| 2017/0014045 A1 | 1/2017 | Tonar et al. |
| 2017/0156658 A1 | 6/2017 | Maharbiz et al. |
| 2017/0172489 A1 | 6/2017 | Afentakis |
| 2017/0188841 A1 | 7/2017 | Ma et al. |
| 2017/0238849 A1 | 8/2017 | Chapman et al. |
| 2017/0255812 A1 | 9/2017 | Kwon |
| 2017/0311807 A1 | 11/2017 | Fu et al. |
| 2017/0319073 A1 | 11/2017 | DiMaio et al. |
| 2018/0020058 A1 | 1/2018 | Martines et al. |
| 2018/0045725 A1 | 2/2018 | Yoo et al. |
| 2018/0220924 A1 | 8/2018 | Burns et al. |
| 2018/0220953 A1 | 8/2018 | Burns et al. |
| 2018/0220954 A1 | 8/2018 | Burns et al. |
| 2018/0220961 A1 | 8/2018 | Burns et al. |
| 2018/0360344 A1 | 12/2018 | Burns et al. |
| 2019/0000352 A1 | 1/2019 | Everett et al. |
| 2019/0038133 A1 | 2/2019 | Tran |
| 2019/0053751 A1 | 2/2019 | Torres |
| 2019/0060602 A1 | 2/2019 | Tran et al. |
| 2019/0069836 A1 | 3/2019 | Hettrick |
| 2019/0104981 A1 | 4/2019 | Sarrafzadeh et al. |
| 2019/0104982 A1 | 4/2019 | Dunn et al. |
| 2019/0117964 A1 | 4/2019 | Bahrami et al. |
| 2019/0134396 A1 | 5/2019 | Toth et al. |
| 2019/0142333 A1 | 5/2019 | Burns et al. |
| 2019/0147990 A1 | 5/2019 | Burns et al. |
| 2019/0148901 A1 | 5/2019 | Komoto |
| 2019/0150882 A1 | 5/2019 | Maharbiz et al. |
| 2019/0175098 A1 | 6/2019 | Burns et al. |
| 2019/0192066 A1 | 6/2019 | Schoess et al. |
| 2019/0246972 A1 | 8/2019 | Burns et al. |
| 2019/0282436 A1 | 9/2019 | Douglas et al. |
| 2019/0290189 A1 | 9/2019 | Sarrafzadeh et al. |
| 2019/0307360 A1 | 10/2019 | Tonar et al. |
| 2019/0307405 A1 | 10/2019 | Terry et al. |
| 2020/0008299 A1 | 1/2020 | Tran et al. |
| 2020/0043607 A1 | 2/2020 | Zerhusen et al. |
| 2020/0069240 A1 | 3/2020 | Burns |
| 2020/0069241 A1 | 3/2020 | Burns |
| 2020/0069242 A1 | 3/2020 | Burns et al. |
| 2020/0077892 A1 | 3/2020 | Tran |
| 2020/0078499 A1 | 3/2020 | Gadde et al. |
| 2020/0093395 A1 | 3/2020 | Tonar et al. |
| 2020/0100723 A1 | 4/2020 | Burns |
| 2020/0113488 A1 | 4/2020 | Al-Ali et al. |
| 2020/0127398 A1 | 4/2020 | Burns et al. |
| 2020/0296821 A1 | 9/2020 | Trublowski et al. |
| 2020/0297244 A1 | 9/2020 | Brownhill et al. |
| 2020/0297255 A1 | 9/2020 | Martinez et al. |
| 2022/0287584 A1 | 9/2022 | Burns et al. |

FOREIGN PATENT DOCUMENTS

| | | |
|---|---|---|
| CA | 2609842 C | 10/2016 |
| CN | 204119175 U | 1/2015 |
| CN | 104352230 A | 2/2015 |
| CN | 104567657 A | 4/2015 |
| CN | 105963074 A | 9/2016 |
| CN | 208111467 U | 11/2018 |
| DE | 102012011212 A1 | 12/2012 |
| EP | 1080687 A1 | 3/2001 |
| EP | 1372475 B1 | 1/2004 |
| EP | 1569553 A1 | 9/2005 |
| EP | 3092946 A1 | 11/2016 |
| EP | 3280488 B1 | 12/2018 |
| GB | 2584808 A | 12/2020 |
| JP | 2001-178705 | 7/2001 |
| JP | 2003-169788 A | 6/2003 |
| JP | 2003-290166 A | 10/2003 |
| JP | 2005-52227 | 3/2005 |
| JP | 2009-268611 A | 11/2009 |

(56) References Cited

FOREIGN PATENT DOCUMENTS

| | | |
|---|---|---|
| JP | 4418419 | 2/2010 |
| JP | 2013-198639 A | 10/2013 |
| KR | 10-2014-0058445 | 5/2014 |
| WO | 1996/010951 A1 | 4/1996 |
| WO | 2001/054580 A1 | 8/2001 |
| WO | 2002/080770 A1 | 10/2002 |
| WO | 2004/105602 A1 | 12/2004 |
| WO | 2006/029035 A1 | 3/2006 |
| WO | 2007/098762 A1 | 9/2007 |
| WO | 2009/144615 A1 | 12/2009 |
| WO | 2010/060102 A2 | 5/2010 |
| WO | 2011/004165 A1 | 1/2011 |
| WO | 2011/022418 A2 | 2/2011 |
| WO | 2011/080080 A1 | 7/2011 |
| WO | 2011/080262 A1 | 7/2011 |
| WO | 2011/091517 A1 | 8/2011 |
| WO | 2011/143071 A2 | 11/2011 |
| WO | 2013/116242 A2 | 8/2013 |
| WO | 2014/186894 A1 | 11/2014 |
| WO | 2015/003015 A2 | 1/2015 |
| WO | 2015/077838 A1 | 6/2015 |
| WO | 2015/168720 A1 | 11/2015 |
| WO | 2015/169911 A1 | 11/2015 |
| WO | 2015/195720 A1 | 12/2015 |
| WO | 2016/172263 A1 | 10/2016 |
| WO | 2016/172264 A1 | 10/2016 |
| WO | 2017/032393 | 3/2017 |
| WO | 2017/214188 A1 | 12/2017 |
| WO | 2017/218818 A2 | 12/2017 |
| WO | 2018/071715 A1 | 4/2018 |
| WO | 2018/077560 A1 | 5/2018 |
| WO | 2018/115461 A1 | 6/2018 |
| WO | 2018/144938 | 8/2018 |
| WO | 2018/144941 | 8/2018 |
| WO | 2018/144943 | 8/2018 |
| WO | 2018/144946 | 8/2018 |
| WO | 2018/189265 A1 | 10/2018 |
| WO | 2018/209100 A1 | 11/2018 |
| WO | 2018/234443 A1 | 12/2018 |
| WO | 2018/236739 | 12/2018 |
| WO | 2019/020551 A1 | 1/2019 |
| WO | 2019/030384 A2 | 2/2019 |
| WO | 2019/048624 A1 | 3/2019 |
| WO | 2019/048626 A1 | 3/2019 |
| WO | 2019/048638 A1 | 3/2019 |
| WO | 2019/072531 A1 | 4/2019 |
| WO | 2019/073389 A1 | 4/2019 |
| WO | 2019/076967 A2 | 4/2019 |
| WO | 2019/096828 A1 | 5/2019 |
| WO | 2019/099810 A1 | 5/2019 |
| WO | 2019/099812 A1 | 5/2019 |
| WO | 2019/113481 | 6/2019 |
| WO | 2019/157290 | 8/2019 |
| WO | 2019/162272 A1 | 8/2019 |
| WO | 2020/014779 A1 | 1/2020 |
| WO | 2020/043806 A1 | 3/2020 |
| WO | 2020/053290 A1 | 3/2020 |
| WO | 2020/077100 A1 | 4/2020 |
| WO | 2020/187643 A1 | 9/2020 |
| WO | 2020/187851 A1 | 9/2020 |
| WO | 2020/234429 A2 | 11/2020 |

OTHER PUBLICATIONS

U.S. Appl. No. 17/700,888, filed Mar. 22, 2022, which is pending.
U.S. Appl. No. 16/695,067, filed Nov. 25, 2019, which issued as U.S. Pat. No. 11,534,077 dated Dec. 27, 2022.
U.S. Appl. No. 16/440,743, filed Jun. 13, 2019, which issued as U.S. Pat. No. 11,284,810 dated Mar. 29, 2022.
U.S. Appl. No. 15/280,528, filed Sep. 29, 2016, which issued as U.S. Pat. No. 9,763,596 dated Sep. 19, 2017.
U.S. Appl. No. 15/280,487, filed Sep. 29, 2016, which issued as U.S. Pat. No. 10,485,447 dated Nov. 26, 2019.
U.S. Appl. No. 15/273,202, filed Sep. 22, 2016, which issued as U.S. Pat. No. 10,178,961 dated Jan. 15, 2019.
U.S. Appl. No. 15/134,110, filed Apr. 20, 2016, which issued as U.S. Pat. No. 10,182,740 dated Jan. 22, 2019.
Alanen, "Measurement of Hydration in the Stratum Corneum with the MoistureMeter and Compairson with the Corneometer," *Skin Research and Technology*, 10:32-37 (2004).
Alberts et al., "The Extracellular Matrix of Animals," Molecular Biology of the Cell, 4th ed., pp. 1065-1127 (2002).
Allman et al., "Pressure Ulcer Risk Factors Among Hospitalized Patients with Activity Limitation," *JAMA*, 273:865-870 (1995).
Anonymous, "Recommended Practices for Positioning the Patient in the Perioperative Practice Setting," in *Perioperative Standards, Recommended Practices, and Guidelines*, AORN, Inc., 525-548 (2006).
Arao et al., "Morphological Characterisitic of the Dermal Papillae In the Development of Pressure," *World Wide Wounds*, (Mar. 1999), 6 pages (obtained online).
Australian Intellectual Property Office, Office Action dated May 1, 2014, for corresponding Australian patent application No. 2011253253 (pp. 1-10) and pending claims (pp. 11-15) pp. 1-15.
Australian Patent Office, Office Action dated Jun. 1, 2015 for corresponding Australian Patent Application No. 2011253253 (pp. 1-4) and claims (pp. 5-10) pp. 1-10.
Bader et al., "Effect of Externally Applied Skin Surface Forces on Tissue Vasculature," *Archives of Physical Medicine and Rehabilitation*, 67(11):807-11 (1986).
Barnes, "Moisture Meters for Use on Thin Lumber and Veneers," *Moisture Register Co.*, 1-5 (1956).
Bates-Jensen et al., "Subepidermal Moisture Predicts Erythema and Stage I Pressure Ulcers in Nursing Homes Residents: A Pilot Study," Journal of the American Geriatric Society, 55:1199-1205 (2007).
Bates-Jensen et al., "Superidermal moisture differentiates erythema and stage 1 pressure ulcers in nursing home residents," Wound Repair Regeneration, 16:189-197 (2008).
Bates-Jensen et al., "Subidermal Moisture Is Associated with Early Pressure Ulcer Damage in Nursing Home Residents with Dark Skin Tones; Pilot Findings," Journal of Wound Ostomy and Continence Nursing, 36(3):277-284 (2009).
Bates-Jensen et al., "Subidermal Moisture Detection of Pressure Induced Tissue Damage on the Trunk: The Pressure Ulcer Detection Study Outcomes," Wound Repair and Regeneration, 25:502-511 (2017).
Berggren, "Capacitive Biosensors," Electroanalysis, 13(3):173-180 (2001), Wiley-VCH (publisher), Weinheim, Germany.
Bergstrand et al., "Pressure-induced Vasodilation and Reactive Hyperemia at Different Depths in Sacral Tissue Under Clinically Relevant Conditions," Microcirculation, 21:761-771 (2014).
Bergstrom et al., "Pressure Ulcers in Adults: Prediction and Prevention," Clinical Practice Guideline—Quick Reference Guide for Clinicians, 117 (1992).
Black et al., "Differential Diagnosis of Suspected Deep Tissue Injury," *International Wound Journal*, 13(4):531-539 (2015).
Brem et al., "Protocol for the Successful Treatment of Pressure Ulcers," *The American Journal of Surgery*, 188 (Suppl. To Jul. 2004):9S-17S (2004).
Brem et al., "High cost of stage IV pressure ulcers," American Journal of Surgery, 200:473-477 (2010).
Brienza et al., "Friction-Induced Skin Injuries-Are They Pressure Ulcers?," Journal of Wound Ostomy and Continence Nursing, 42(1):62-64 (2015).
Carmo-Araujo et al., "Ischaemia and reperfusion effects on skeletal muscle tissue: morphological and histochemical studies," International Journal of Experimental Pathology, 88:147-154 (2007).
Ceelen et al., "Comparison-induced damage and internal tissue strains are related," Journal of Biomechanics, 41:3399-3404 (2008).
Ching et al., "Tissue electrical properties monitoring for the prevention of pressure sore," Prosthetics and Orthotics International, 35(4):386-394 (2011).
Clendenin et al., "Inter-operator and inter-device agreement and reliability of the SEM Scanner," Journal of Tissue Viability, 24(1):17-23 (2015).

(56) References Cited

OTHER PUBLICATIONS

De Lorenzo et al., "Predicting body cell mass with bioimpedance by using theoretical methods: a technological review," Journal of Applied Physiology, 82(5):1542-1558 (1997).

de Oliveira et al., "Sub-epidermal moisture versus tradition and visual skin assessments to assess pressure ulcer risk in surgery patients," Journal of Wound Care, 31(3):254-264 (2022), Mark Allen Group (pub.) (obtained online).

Demarre et al., "The cost of pressure ulcer prevention and treatment in hospitals and nursing in Flanders: A cost-of-illness study," International Journal of Nursing Studies, 1-14 (2015).

Dodde et al., "Bioimpedance of soft tissue under compression," Physiology Measurement, 33(6):1095-1109 (2012).

Dupont, "Pyralux® FR Coverlay, Bondply & Sheet Adhesive," webpage, Retrieved from: www2.dupont.com/Pyralux/en_US/products/adhesives_films/FR/FR_films_html pp. 1-2 (2012).

DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).

DuPont, "Pyralux® FR Copper-clad Laminate," webpage, Retrieved from: www2.dupont.com/Pyraluxlen_US/ productsllaminate/FR/pyralux_fr.html, pp. 1-2 (2012).

Eberlein-Gonska et al., "The Incidence and Determinants of Decubitus Ulcers in Hospital Care: An Analysis of Routine Quality Management Data at a University Hospital," Deutsches Arzteblatt International, 110(33-34):550-556 (2013).

European Patent Office, ESSR dated Aug. 22, 2014, for corresponding European Patent Application No. 11781061.4 (pp. 1-7) and pending claims (pp. 3-10) pp. 1-10.

European Patent Office, Office Action dated Jul. 13, 2015, for corresponding European Patent Application No. 11781061.4 (pp. 1-5) and claims (pp. 6-9) pp. 1-9.

Extended European Search Report dated Aug. 30, 2016, in European Patent Application No. 16169670.

Extended European Search Report dated Oct. 18, 2016, in European Patent Application No. 16166483.4.

Extended European Search Report dated Mar. 13, 2017, in European Patent Application No. 16196899.5.

Extended European Search Report dated Oct. 25, 2019, in European Patent Application No. 19186393.5.

Extended European Search Report dated Nov. 19, 2019, in European Patent Application No. 19190000.0.

Extended European Search Report dated Feb. 6, 2020, in European Patent Application No. 18748733.5.

Extended European Search Report dated Feb. 10, 2020, in European Patent Application No. 18748025.6.

Extended European Search Report dated Feb. 10, 2020, in European Patent Application No. 18748512.3.

Extended European Search Report dated Jun. 24, 2020, in European Patent Application No. 18747707.0.

Extended European Search Report dated Mar. 17, 2022, in European Patent Application No. 19838240.0.

Extended European Search Report dated May 24, 2022, in European Patent Application No. 19871332.3.

Extended European Search Report dated Feb. 1, 2023, in European Patent Application No. 22211200.

Ford, "Hospice Wins Award for Innovation in Pressue Ulcer Prevention," *Nursing Times*, downloaded and printed on Apr. 18, 2020, from https://www.nursingtimes.net/news/research-and-innovation/hospice-wins-award-for-innovation-in-pressure-ulcer-prevention-30-11-2018/ (2018).

Gabriel et al., "The dielectric properties of biological tissues: II. Measurements in the frequency range 10 Hz to 20 GHz," Physics in Medicine and Biology, 41:2251-69 (1996).

Gabriel, "Compilation of the Dielectric Properties of Body Tissues at Rf and Microwave Frequencies Report," Occupational and Environmental Health Directorate, (1996).

Gardiner et al., "Incidence of hospital-acquired pressure ulcers—a population-based cohort study," International Wound Journal, 11(6):696-700 (2014).

Gershon et al., "SEM Scanner Readings to Assess Pressure Induced Tissue Damage," Proceedings pf the 17th Annual European Pressure Ulcer Advisory Panel (EPUAP) meeting, Stockholm, Sweden (2014).

Gonzalez-Correa et al., "Electrical bioimpedance readings increase with higher pressure applied to the measuring probe," Physiology Measurement, 26:S39-S47 (2005).

Great Britain Search Report dated Apr. 27, 2020, in Great Britian Patent Application No. GB2002889.0.

Great Britain Search Report dated Jun. 28, 2021, in Great Britian Patent Application No. GB2106848.1

Great Britain Search Report dated Feb. 9, 2022, in Great Britian Patent Application No. GB2118088.0.

Great Britain Search Report dated Feb. 14, 2022, in Great Britian Patent Application No. GB2118092.2.

Guihan et al., "Assessing the feasibility of subepidermal moisture to predict erythema and stage 1 pressure ulcers in persons with spinal cord injury: A pilot study," Journal of Spinal Cord Medicine, 35(1):46-52 (2012).

Hamazoto et al., "Estimate of Burn Depth by Non-Invasive Capacitance Measurement," *Japan Soc. ME & BE*, 42:266 (Jun. 2003).

Harrow, "Subepidermal moisture surrounding pressure ulcers in persons with a spinal cord injury: A pilot study," Journal of Spinal Cord Medicine, 37(6):719-728 (2014).

Hou, "Section IV. Osteofasical Compartment Syndrome," Limbs Trauma, 7:215-217 (2016), Hubei Science & Technology Publishing House (pub.), Wuhan, China.

Houwing et al., "Pressure-induced skin lesions in pigs: reperfusion injury and the effects of vitamin E," Journal of Wound Care, 9(1):36-40 (2000).

Huang et al., "A device for skin moisture and environment humidity detection," Sensors and Actuators B: Chemical, 206-212 (2008).

International Search Report and Written Opinion dated Apr. 20, 2016 for International Patent Application No. PCT/US2016/28515.

International Search Report and Written Opinion dated Feb. 9, 2012 for International Patent Application No. PCT/US2011/035618.

International Search Report and Written Opinion dated Jul. 22, 2016 for International Patent Application No. PCT/US2016/28515.

International Search Report and Written Opinion dated Jul. 26, 2016 for International Patent Application No. PCT/US2016/28516.

International Search Report dated Apr. 12, 2018 issued in International Patent Application No. PCT/US2018/016731.

International Search Report dated Apr. 12, 2018 issued in International Patent Application No. PCT/US2018/016738.

International Search Report dated Apr. 26, 2018 issued in International Patent Application No. PCT/US2018/016741.

International Search Report dated Jul. 12, 2018 issued in International Patent Application No. PCT/US2018/016736.

International Search Report dated Sep. 10, 2018 issued in International Patent Application No. PCT/US2018/038055.

International Search Report dated Jan. 29, 2019 issued in International Patent Application No. PCT/US2018/061494.

International Search Report dated Feb. 5, 2019 issued in International Patent Application No. PCT/US2018/064527.

International Search Report dated Feb. 11, 2019 issued in International Patent Application No. PCT/US2018/061497.

International Search Report dated May 29, 2019 issued in International Patent Application No. PCT/US2019/017226.

International Search Report dated Mar. 9, 2020 issued in International Patent Application No. PCT/US2019/055655.

International Search Report dated Dec. 8, 2020 issued in International Patent Application PCT/US2020/051134.

International Search Report dated Aug. 17, 2021 issued in International Patent Application PCT/US2021/023818.

International Search Report dated May 13, 2022 issued in International Patent Application PCT/US2022/014913.

International Search Report dated Aug. 2, 2022 issued in International Patent Application PCT/US2022/025508.

International Search Report dated Aug. 15, 2022 issued in International Patent Application PCT/US2022/019338.

(56) References Cited

OTHER PUBLICATIONS

Jan et al., "Local cooling reduces skin ischemia under surface pressure in rats: as assessment by wavelet analysis of laser Doppler blood flow oscillations," Physiology Measurement, 33(10):1733-1745 (2012).
Jaskowski, "Evaluation of the Healing Process of Skin Wounds by Means of Skin Absolute Value of Electrical Impedance," *Dermatol. Mon.schr.*, 172(4):223-228 (1986).
Jiang et al., "Ischemia-Reperfusion Injury-Induced Histological Changes Affecting Early Stage Pressure Ulcer Development in a Rat model," Ostomy Wound Management, 57:55-60 (2011).
Jiang et al., "Expression of cytokines, growth factors and apoptosis-related signal molecules in chronic pressure ulcer wounds healing," Spinal Cord, 52(2):145-151 (2014).
Jiricka et al., "Pressure Ulcer Risk factors in an ICU Population," American Journal of Crital Care, 4:361-367 (1995).
Kanai et al., "Electrical measurement of fluid distribution in legs and arms," Medical Progress through Technology Journal, 12:159-170 (1987).
Kasuya et al., "Potential application of in vivo imaging of impaired lymphatic duct to evaluate the severity of pressure ulcer in mouse model," Scientific Reports, 4:4173 (7 pages) (2014).
Lee, "CapSense Best Practices," Application Note 2394, 1-10 (2007).
Liu et al., "A Systematic Review of Electrical Stimulation for Pressure Ulcer Prevention and Treatment in People with Spinal Cord Injuries," *The Journal of Spinal Cord Medicine*, 37(6):703-718 (2014).
Loerakker et al., "Temporal Effects of Mechanical Loading on Deformation-Induced Damage in Skeletal Muscle Tissue," Annual Review of Biomedical Engineering, 38(8):2577-2587 (2010).
Loerakker et al., "The effects of deformation, ischemia, and reperfusion on the development of muscle damage during prolonged loading," Journal of Applied Physiology, 111(4):1168-1177 (2011).
Lyder et al., "Quality of Care for Hospitalized Medicare Patients at Risk for Pressure Ulcers," Archives of Internal Medicine, 161:1549-1554 (2001).
Martinesen, "Bioimpedance and Bioelectricity Basics," Elsevier Academic Press, Chapters 1 and 10 (2015).
Mathiesen et al., "Are labour-intensive efforts to prevent pressure ulcers cost-effective?" Journal of Medicine Economics, 16(10):1238-1245 (2013).
Matthie et al., "Analytic assessment of the various bioimpedance methods used to estimate body water," Journal of Applied Physiology, 84(5):1801-1816 (1998).
Miller et al., "Lymphatic Clearance during Compressive Loading," Lymphology, 14(4):161-166 (1981).
Moore et al., "A randomised controlled clinical trial of repositioning, using the 30° tilt, for the prevention of pressure ulcers," Journal of Clinical Nursing, 20:2633-2644 (2011).
Moore et al., "Pressure ulcer prevalence and prevention practices in care of the older person in the Republic of Ireland," Journal of Clinical Nursing, 21:362-371 (2012).
Moore et al., "A review of PU prevalence and incidence across Scandinavia, Iceland and Ireland (Part I)", Journal of Wound Care, 22(7):361-362, 364-368 (2013).
Moore et al., "Subepidermal Moisture (SEM) and Bioimpedance: A Literature Review of a Novel Method for Early Detection of Pressure-Induced Tissue Damage (Pressure Ulcers)," *International Wound Journal*, 14(2):331-337 (2016).
Moore, "Using SE, (Sub Epidermal Moisture) Measurement for Early Pressure Ulcer Detection," Institute for Pressure Injury Prevention, WCICT 2017 (Jun. 20-21), Manchester, UK, 7 pp., available at www.pressureinjuryprevention.com/wp-content/uploads/2017/07/ipip_Moore_Sub_Epidermal_Moisture_notes.pdf (2017) (obtained online).
Moore et al., "SEM Scanner Made Easy," *Wounds International*, pp. 1-6, available at www.woundsinternational.com (2018).

Mulasi, "Bioimpedance at the Bedside: Current Applications, Limitations, and Opportunities," Nutritional Clinical Practice, 30(2):180-193 (2015).
Musa et al., "Clinical impact of a sub-epidermal moisture scanner: what is the real-world use?," J. Wound Care, 30(3):2-11 (2012), Mark Allen Group (pub.) (obta
National Pressure Ulcer Advisory Panel et al., "Prevention and Treatment of Pressure Ulcers: Clinical Practice Guideline," Cambridge Media, (2014).
Nixon et al., "Pathology, diagnosis, and classification of pressure ulcers: comparing clinical and imaging techniques," Wound Repair and Regeneration, 13(4):365-372 (2005).
Nuutinen et al., "Validation of a new dielectric device to assess changes of tissue water in skin and subcutaneous fat," Physiological Measurement, 25:447-454 (2004).
O'Goshi, "Skin conductance; validation of Skicon-200EX compared to the original model, Skicon-100," Skin Research and Technology, 13:13-18 (2007).
Oliveira, "The Accuracy of Ultrasound, Thermography, Photography and Sub-Epidermal Moisture as a Predictor of Pressure Ulcer Presence—a Systematic Review," RCSI, School of Nursing thesis (2015).
Oomens et al., "Pressure Induced Deep Tissue Injured Explained," Annual Review of Biomedical Engineering, 43(2):297-305 (2015).
Ousey et al., "Diabetic Foot or Pressure Ulcer on the Foot?," *Wounds UK*, 7(3):105-108 (2007).
Pang et al. (eds.) *Diagnosis and Treatment of Diabetes,* China Pres of Traditional Chinese Medicine (publisher), Beijing, China, pp. 466-468 (Oct. 2016), with English Translation.
Rotaru et al., "Friction between Human Skin and Medical Textiles for Decubitus Prevention," *Tribology International,* 65:91-96 (2013).
Saxena, *The Pocket Doctor: Obstetrics & Gynecology*, pp. 76-77 (2017), Tianjin Science & Technology Translation & Publishing Co. Ltd. (publ.), Tianjin, China.
Scallan et al., "Chapter 4: Pathophysiology of Edema Formation," Capillary Fluid Exhange: Regulation, Functions, and Pathology, 47-61 (2010).
Schultz et al., "Extracellular matrix: review of its role in acute and chronic wounds," World Wide Wounds, 1-20 (2005).
Schwan, "Electrical properties of tissues cells," Advances in Biology and Medical Physics, 15:148-199 (1957).
Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151, 44 pp. (Aug. 2019).
Sener et al., "Pressure ulcer-induced oxidative organ injury is ameliorated by beta-glucan treatment in rats," International Immunopharmacology, 6(5):724-732 (2006).
Sewchuck et al., "Prevention and Early Detection of Pressure Ulcers in Patients Undergoing Cardiac Surgery," AORN Journal, 84(1):75-96 (2006).
Sprigle et al., "Analysis of Localized Erythema Using Clinical Indicators and Spectroscopy," Ostomy Wound Management, 49:42-52 (2003).
Stekelenburg et al., "Role of ischemia and deformation in the onset of compression-induced deep tissue injury: MRI-based studies in a rat model," Journal of Applied Physiology, 102:2002-2011 (2007).
Stekelenburg et al., "Deep Tissue Injury: How Deep is Our Understanding?" Archives of Physical Medicine Rehabilitation Medicine Rahabilitation, 89(7):1410-1413 (2008).
Supplementary Partial European Search Report dated Jan. 27, 2020, in European Patent Application No. 18747707.
Supplementary European Search Report dated Jul. 13, 2021, in European Patent Application No. 18887039.
Supplementary European Search Report dated Oct. 1, 2021, in European Patent Application No. 19751130.
Swisher et al., "Impedance sensing device enables early detection of pressure ulcers in vivo," Nature Communications, 6:6575-6584 (2014).

(56) References Cited

OTHER PUBLICATIONS

Thomas et al., "Hospital-Acquired Pressure Ulcers and Risk of Death," Journal of the American Geriatrics Society, 44:1435-1440 (1996).

Thomas, "Prevention and Treatment of Pressure Ulcers," *J. Am. Med. Dir. Assoc.*, 7:46-59 (2006).

Truong et al., "Pressure Ulcer Prevention in the Hospital Setting Using Silicone Foam Dressings," *Cureus*, 8(8):e730, pp. 1-6 (2016).

Tur et al., "Topical Hydrogen Peroxide Treatment of Ischemic Ulcers in the Guinea Pig: Blood Recruitment in Multiple Skin Sites," *J. Am Acad. Dermatol.*, 33:217-221 (1995).

Valentinuzzi et al., "Bioelectrical Impedance Techniques in Medicine. Part II: Monitoring of Physiological Events by Impedance," Critical Reviews in Biomedical Engineering, 24(4-6):353-466 (1996).

Vangilder et al., "Results of Nine International Pressure Ulcer Prevalence Surveys: 1989 to 2005," Ostomy Wound Management, 54(2):40-54 (2008).

Vowden et al., "Diabetic Foot Ulcer or Pressure Ulcer? That Is the Question," *The Diabetic Foot Journal*, 18:62-66 (2015).

Wagner et al., "Bioelectrical Impedance as a Discriminator of Pressure Ulcer Risk," Advances in Wound Care, 9(2):30-37 (1996).

Wang et al., "A Wireless Biomedical Instrument for Evidence-Based Tissue Wound Characterization," *Wireless Health*, pp. 222-223 (2010).

Wang, "Biomedical System for Monitoring Pressure Ulcer Development," UCLA Electronic Theses and Dissertations, California, USA, pp. 1-123 (2013).

Watanabe et al., "CT analysis of the use of the electrical impedance technique to estimate local oedema in the extremities in patients with lymphatic obstruction," Medical and Biological Engineering and Computing, 36(1):60-65 (1998).

Weiss, "Tissue destruction by neutrophils," The New England Journal of Medicine, 36(1):60-65 (1998).

Yang, *Handbook of Practical Burn Surgery*, p. 48 (2008), People's Military Medical Press (publ.), Beijing, China.

Zanibbi, "Pattern Recognition: An Overview," downloaded from https://www.cs.rit.edu/~rlaz/prec20092/slides/Overview/pdf, 33 pp. (2010).

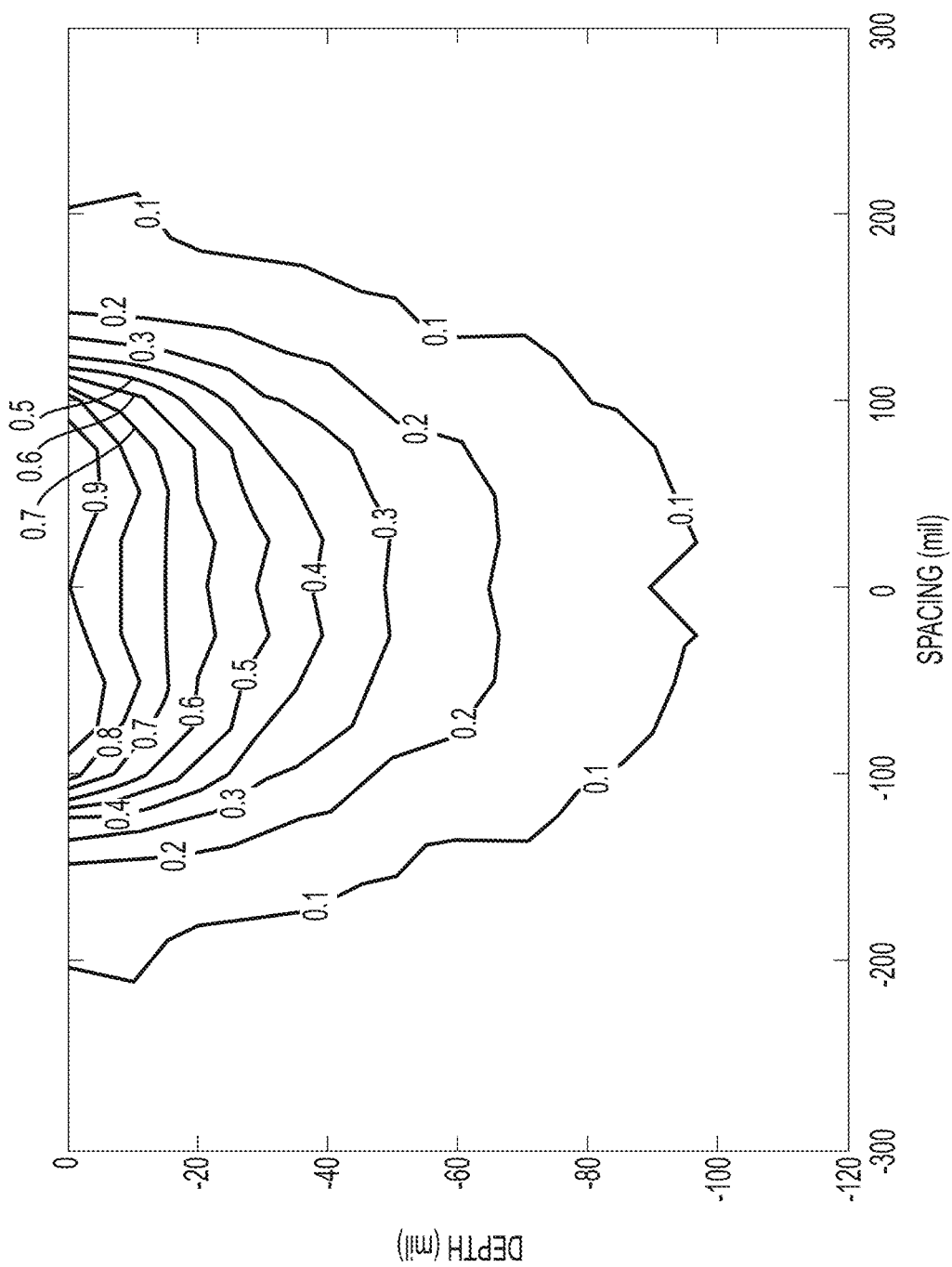

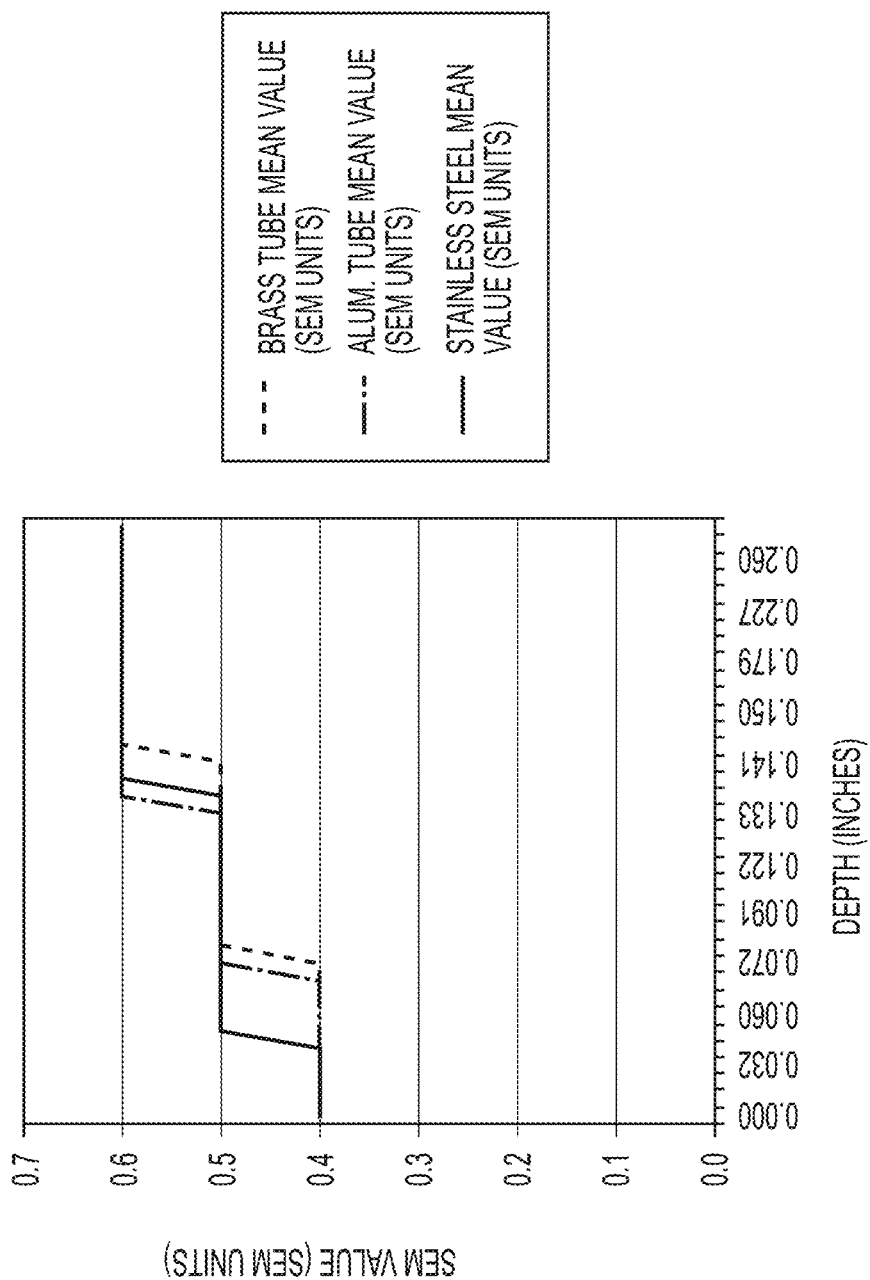

APPARATUS AND METHODS FOR DETERMINING DAMAGED TISSUE USING SUB-EPIDERMAL MOISTURE MEASUREMENTS

RELATED CASES

This application is a continuation of U.S. application Ser. No. 17/700,888 filed Mar. 22, 2022, which is a continuation of Ser. No. 16/440,743 filed Jun. 13, 2019 (now U.S. Pat. No. 11,284,810 issued Mar. 29, 2022), which is a continuation of U.S. application Ser. No. 15/280,487, filed Sep. 29, 2016 (now U.S. Pat. No. 10,485,447 issued Nov. 26, 2019), and U.S. application Ser. No. 15/280,528, filed Sep. 29, 2016 (now U.S. Pat. No. 9,763,596 issued Jan. 19, 2017), which are continuations of U.S. application Ser. No. 15/273,202, filed Sep. 22, 2016 (now U.S. Pat. No. 10,178,961, issued Jan. 15, 2019), which is a continuation of U.S. application Ser. No. 15/134,110, filed Apr. 20, 2016 (now U.S. Pat. No. 10,182,740, issued Jan. 22, 2019), which claims priority to U.S. Provisional Application Ser. No. 62/152,549, filed Apr. 24, 2015, the entirety of each of which is incorporated by reference herein. All references referred to herein are herein incorporated by reference in their entireties.

FIELD OF INVENTION

The present disclosure provides apparatuses and computer readable media for measuring sub-epidermal moisture in patients to determine damaged tissue for clinical intervention. The present disclosure also provides methods for determining damaged tissue.

BACKGROUND

The skin is the largest organ in the human body. It is readily exposed to different kinds of damages and injuries. When the skin and its surrounding tissues are unable to redistribute external pressure and mechanical forces, pressure ulcers may be formed. Pressure ulcers pose a significant health and economic concern internationally, across both acute and long-term care settings. Pressure ulcers impact approximately 2.5 million people a year in the United States and an equivalent number in the European Union. In long-term and critical care settings, up to 25% of elderly and immobile patients develop pressure ulcers. Approximately 60,000 U.S. patients die per year due to infection and other complications from pressure ulcers.

Most pressure ulcers occur over bony prominences, where there is less tissue for compression and the pressure gradient within the vascular network is altered. Pressure ulcers are categorized in one of four stages, ranging from the earliest stage currently recognized, in which the skin remains intact but may appear red over a bony prominence (Stage 1), to the last stage, in which tissue is broken and bone, tendon or muscle is exposed (Stage 4). Detecting pressure ulcers before the skin breaks and treating them to avoid progression to later stages is a goal of policy makers and care providers in major economies. Most pressure ulcers are preventable, and if identified before the first stage of ulceration, deterioration of the underlying tissue can be halted.

Of the four main stages of pressure ulcers, the earliest stage currently recognized (Stage 1) is the least expensive to treat at an average of $2,000 per ulcer, but is also the hardest to detect. In many cases, injuries on the epidermis layer are not present or apparent when the underlying subcutaneous tissue has become necrotic. As a result, it is common that a clinician's first diagnosis of a pressure ulcer in a patient occurs at late stages of the ulcer development—at which time the average cost of treatment is $43,000 per Stage 3 ulcer, or $129,000 per Stage 4 ulcer. If clinicians could identify and diagnose pressure ulcers at earlier stages of ulcer development, the healing process would be considerably shortened and the treatment costs would be significantly lower.

To treat pressure ulcers in a timely and effective manner, clinicians need to be able to identify, with precision, the ulceration area. However, the current standard to detect pressure ulcers is by visual inspection, which is subjective, unreliable, untimely, and lacks specificity.

SUMMARY OF THE INVENTION

In an aspect, the present disclosure provides for, and includes, an apparatus for identifying damaged tissue. The apparatus may comprise one or more electrodes capable of interrogating tissue at and around an anatomical site, where each of the one or more electrodes may be configured to emit and receive a radiofrequency signal to generate a bioimpedance signal; a circuit that may be electronically coupled to the one or more electrodes and may be configured to convert the bioimpedance signal into a sub-epidermal moisture ("SEM") value; a processor that may be electronically coupled to the circuit and may be configured to receive the SEM value; and a non-transitory computer readable medium that may be electronically coupled to the processor and may comprise instructions stored thereon that, when executed on the processor, may perform the steps of receiving from the processor a SEM value measured at the anatomical site and at least two SEM values measured around the anatomical site and their relative measurement locations; determining a maximum SEM value from the measurements around the anatomical site; determining a difference between the maximum SEM value and each of the at least two SEM values measured around the anatomical site; and flagging the relative measurement locations associated with a difference greater than a predetermined value as damaged tissue. In another aspect, a difference is determined between the maximum SEM value and a minimum SEM value measured around the anatomical site.

In yet another aspect, the apparatus may comprise one or more electrodes capable of interrogating tissue at and around an anatomical site, where each of the one or more electrodes may be configured to emit and receive a radiofrequency signal to generate a bioimpedance signal; a circuit that may be electronically coupled to the one or more electrodes and may be configured to convert the bioimpedance signal into a SEM value; a processor that may be electronically coupled to the circuit and may be configured to receive the SEM value; and a non-transitory computer readable medium that may be electronically coupled to the processor and may comprise instructions stored thereon that, when executed on the processor, may perform the steps of receiving from the processor a SEM value measured at the anatomical site and at least two SEM values measured around the anatomical site and their relative measurement locations; determining an average SEM value for each group of SEM values measured at approximately equidistance from the anatomical site; determining a maximum SEM value from the average SEM values; determining a difference between the maximum average SEM value and each of the average SEM values measured around the anatomical site; and flagging the relative measurement locations associated with a difference greater than a predetermined value as damaged tissue.

In yet another aspect, the present disclosure provides for, and includes, a non-transitory computer readable medium for identifying damaged tissue. The non-transitory computer readable medium may comprise instructions stored thereon, that when executed on a processor, may perform the steps of receiving a SEM value at an anatomical site and at least two SEM values measured around the anatomical site and their relative measurement locations; determining a maximum SEM value from the measurements around the anatomical site, determining a difference between the maximum SEM value and each of the at least two SEM values measured around the anatomical site; and flagging the relative measurement locations associated with a difference greater than a predetermined value as damaged tissue. In another aspect, a difference is determined between the maximum SEM value and a minimum SEM value measured around the anatomical site.

In another aspect, the non-transitory computer readable medium may comprise instructions stored thereon that when executed on a processor, may perform the steps of receiving a SEM value at an anatomical site, and at least two SEM values measured around the anatomical site and their relative measurement locations; determining an average SEM value for each group of SEM values measured at approximately equidistance from the anatomical site; determining a maximum SEM value from the average SEM values; determining a difference between the maximum average SEM value and each of the average SEM values measured around the anatomical site; and flagging the relative measurement locations associated with a difference greater than a predetermined value as damaged tissue.

In a further aspect, the present disclosure provides for, and includes, methods for identifying damaged tissue. A method according to the present disclosure may comprise measuring at least three sub-epidermal moisture values at and around an anatomical site using an apparatus that may comprise one or more electrodes that may be capable of interrogating tissue at and around an anatomical site, wherein each of the one or more electrodes may be configured to emit and receive a radiofrequency signal to generate a bioimpedance signal; a circuit that may be electronically coupled to the one or more electrodes and configured to convert the bioimpedance signal into a SEM value; a processor that may be electronically coupled to the circuit and configured to receive the SEM value; and a non-transitory computer readable medium that may be electronically coupled to the processor and may comprise instructions stored thereon that when executed on the processor, may perform the steps of receiving from the processor a SEM value measured at the anatomical site and at least two SEM values measured around the anatomical site and their relative measurement locations; determining a maximum SEM value from the measurements around the anatomical site; determining a difference between the maximum SEM value and each of the at least two SEM values measured around the anatomical site; and flagging the relative measurement locations associated with a difference greater than a predetermined value as damaged tissue. In another aspect, a difference is determined between the maximum SEM value and a minimum SEM value measured around the anatomical site. The method may further comprise obtaining the relative measurement locations flagged as damaged tissue from the apparatus.

In another aspect, a method according to the present disclosure may comprise measuring at least three sub-epidermal moisture values at and around an anatomical site using an apparatus that may comprise one or more electrodes that may be capable of interrogating tissue at and around an anatomical site, wherein each of the one or more electrodes may be configured to emit and receive a radiofrequency signal to generate a bioimpedance signal; a circuit that may be electronically coupled to the one or more electrodes and configured to convert the bioimpedance signal into a SEM value; a processor that may be electronically coupled to the circuit and configured to receive the SEM value; and a non-transitory computer readable medium that may be electronically coupled to the processor and may comprise instructions stored thereon that, when executed on the processor, may perform the steps of receiving from the processor a SEM value measured at the anatomical site and at least two SEM values measured around the anatomical site and their relative measurement locations; determining an average SEM value for each group of SEM values measured at approximately equidistance from the anatomical site; determining a maximum SEM value from the average SEM values; determining a difference between the maximum average SEM value and each of the average SEM values measured around the anatomical site; and flagging the relative measurement locations associated with a difference greater than a predetermined value as damaged tissue. The method may further comprise obtaining the relative measurement locations flagged as damaged tissue from the apparatus.

In a further aspect, the present disclosure provides for, and includes, methods for generating a SEM image indicating damaged tissue on an anatomical graphical representation. The SEM image may be generated by acquiring parameters of an anatomical site to be interrogated; measuring at least three sub-epidermal moisture values at and around an anatomical site using an apparatus that may comprise one or more electrodes that may be capable of interrogating tissue at and around an anatomical site, wherein each of the one or more electrodes may be configured to emit and receive a radiofrequency signal to generate a bioimpedance signal; a circuit that may be electronically coupled to the one or more electrodes and configured to convert the bioimpedance signal into a SEM value; a processor that may be electronically coupled to the circuit and configured to receive the SEM value; and a non-transitory computer readable medium that may be electronically coupled to the processor and may comprise instructions stored thereon that when executed on the processor, may perform the steps of receiving from the processor a SEM value measured at the anatomical site, and at least two SEM values measured around anatomical site and their relative measurement locations; determining a maximum SEM value from the measurements around the anatomical site, determining a difference between the maximum SEM value and each of the at least two SEM values measured around the anatomical site; and flagging the relative measurement locations associated with a difference greater than a predetermined value as damaged tissue. In another aspect, a difference is determined between the maximum SEM value and a minimum SEM value measured around the anatomical site. The method may further comprise plotting the measured SEM values in accordance with their relative measurement locations on a graphical representation of an area defined by the parameters of the anatomical site, and indicating the measurement locations that are flagged as damaged tissue.

In yet another aspect, the SEM image may be generated by acquiring parameters of an anatomical site to be interrogated; measuring at least three sub-epidermal moisture values at and around an anatomical site using an apparatus that may comprise one or more electrodes that may be capable of interrogating tissue at and around an anatomical site, wherein each of the one or more electrodes may be configured to emit and receive a radiofrequency signal to generate a bioimpedance signal; a circuit that may be electronically coupled to the one or more electrodes and configured to convert the bioimpedance signal into a SEM value; a processor that may be electronically coupled to the circuit and configured to receive the SEM value; and a non-transitory computer readable medium that may be electronically coupled to the processor and may comprise instructions stored thereon that, when executed on the processor, may perform the steps of receiving from the processor a SEM value measured at the anatomical site, and at least two SEM values measured around anatomical site and their relative measurement locations; determining an average SEM value for each group of SEM values measured at approximately equidistance from the anatomical site; determining a maximum SEM value from the average SEM values; determining a difference between the maximum average SEM value and each of the average SEM values measured around the anatomical site; and flagging the relative measurement locations associated with a difference greater than a predetermined value as damaged tissue. The method may further comprise plotting the measured SEM values in accordance with their relative measurement locations on a graphical representation of an area defined by the parameters of the anatomical site, and indicating the measurement locations that is flagged as damaged tissue.

BRIEF DESCRIPTION OF THE FIGURES

Some aspects of the disclosure are herein described, by way of example only, with reference to the accompanying drawings. With specific reference now to the drawings in detail, it is stressed that the particulars shown are by way of example and are for purposes of illustrative discussion of embodiments of the disclosure. In this regard, the description, taken with the drawings, make apparent to those skilled in the art how aspects of the disclosure may be practiced.

FIG. 12A—A sample graphical representation of a finite element model showing the depth of various SEM levels in accordance with the methods in the present disclosure.

FIG. 12B—A sample plot of SEM measurements at various depth of a skin-like material.

DETAILED DESCRIPTION

Figure 1:
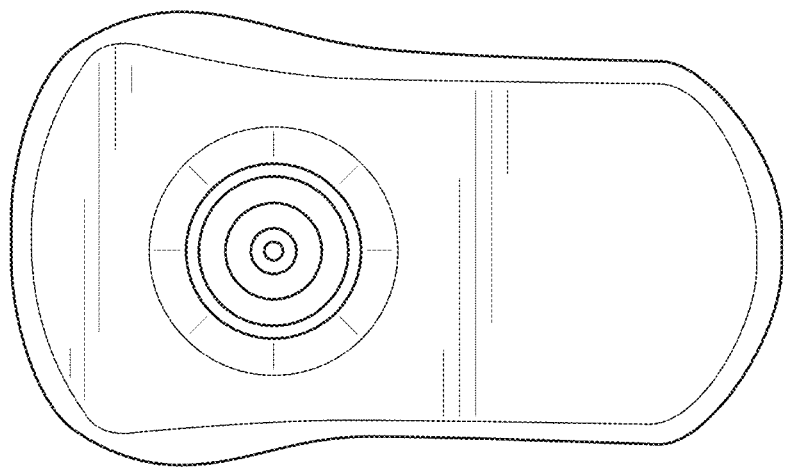
FIG. 1—An exemplary apparatus according to the present disclosure, comprising one coaxial electrode.
Figure 1:
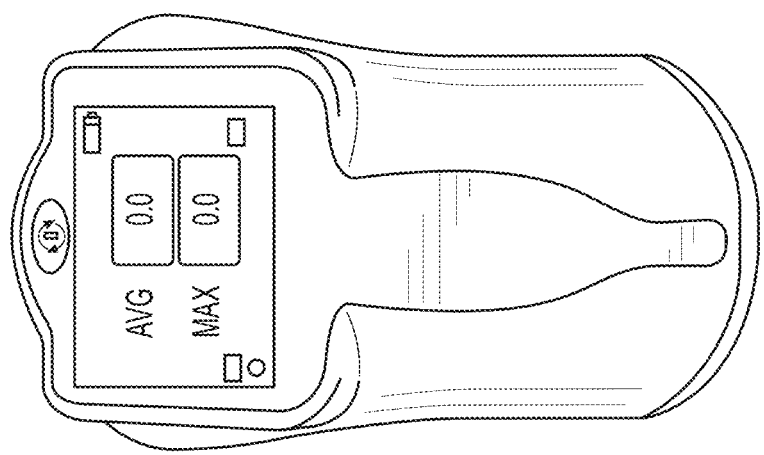

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises," and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed disclosure. Thus, the term "consisting essentially of" when used in a claim of this disclosure is not intended to be interpreted to be equivalent to "comprising."

As used herein, the term "sub-epidermal moisture" refers to the increase in tissue fluid and local edema caused by vascular leakiness and other changes that modify the underlying structure of the damaged tissue in the presence of continued pressure on tissue, apoptosis, necrosis, and the inflammatory process.

As used herein, a "system" may be a collection of devices in wired or wireless communication with each other.

As used herein, "interrogate" refers to the use of radiofrequency energy to penetrate into a patient's skin.

As used herein a "patient" may be a human or animal subject.

Figure 2:
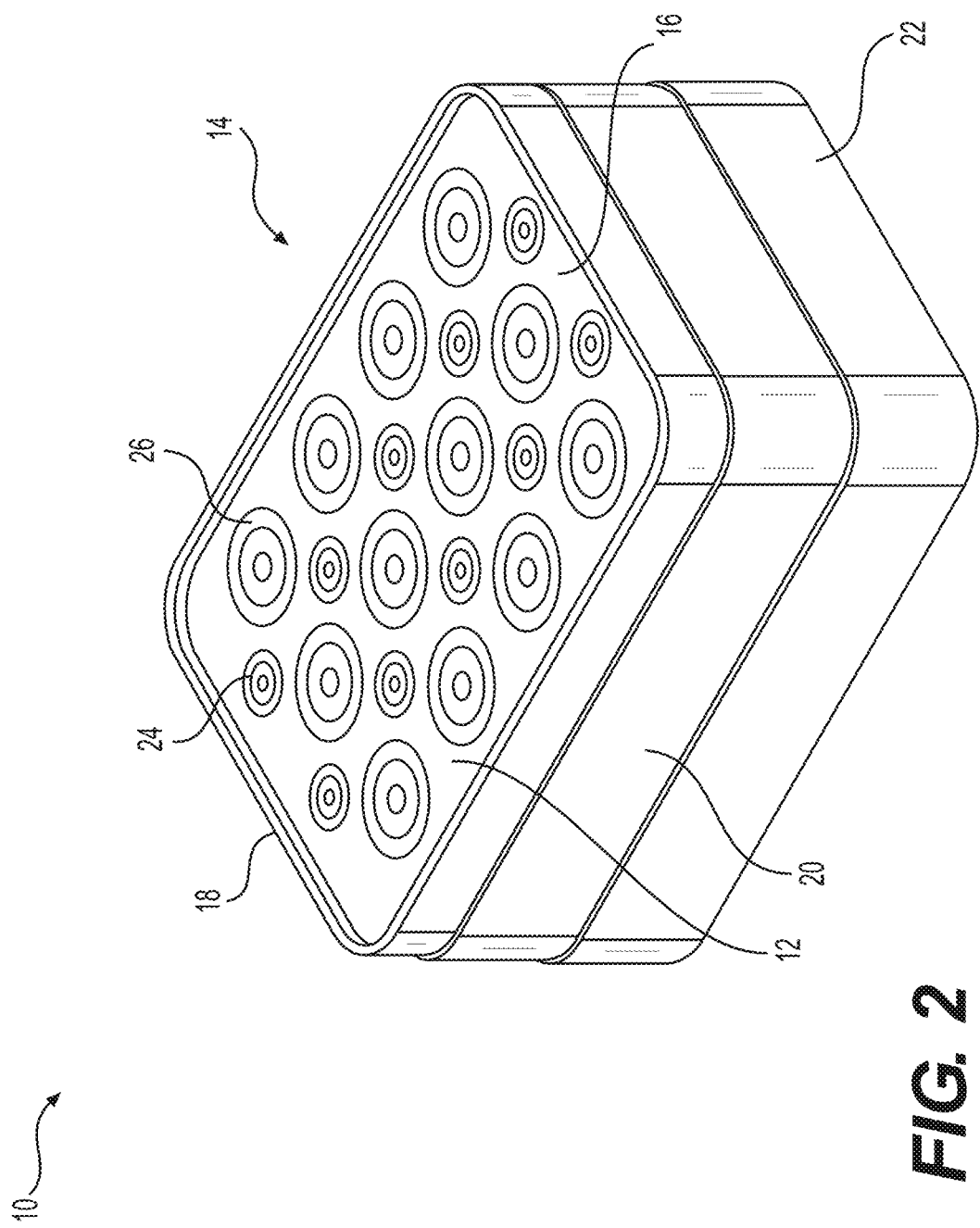
FIG. 2—An exemplary sensing unit of the apparatus according to the present disclosure, comprising more than one coaxial electrode.

An exemplary apparatus according to the present disclosure is shown in FIGS. 1 and 2. It will be understood that these are examples of an apparatus for measuring sub-epidermal moisture ("SEM"). In some embodiments, the apparatus according to the present disclosure may be a handheld device, a portable device, a wired device, a wireless device, or a device that is fitted to measure a part of a human patient. U.S. Publication No. 2014/0288397 A1 to Sarrafzadeh et al. is directed to a SEM scanning apparatus, which is incorporated herein by reference in its entirety.

In certain embodiments according to the present disclosure, the apparatus may comprise one or more electrodes. In one aspect according to the present disclosure, it may be preferable to use coaxial electrodes over electrodes such as tetrapolar ECG electrodes because coaxial electrodes are generally isotropic, which may allow SEM values to be taken irrespective of the direction of electrode placement. The SEM values measured by coaxial electrodes may also be representative of the moisture content of the tissue underneath the coaxial electrodes, rather than the moisture content of the tissue surface across two bi-polar electrodes spaced apart.

In some embodiments, the apparatus may comprise two or more coaxial electrodes, three or more coaxial electrodes, four or more coaxial electrodes, five or more coaxial electrodes, ten or more coaxial electrodes, fifteen or more coaxial electrodes, twenty or more coaxial electrodes, twenty five or more coaxial electrodes, or thirty or more coaxial electrodes. In some embodiments, the aforementioned coaxial electrodes may be configured to emit and receive an RF signal at a frequency of 32 kilohertz (kHz). In other embodiments, the coaxial electrodes may be configured to emit and receive an RF signal at a frequency of from about 5 kHz to about 100 kHz, from about 10 kHz to about 100 kHz, from about 20 kHz to about 100 kHz, from about 30 kHz to about 100 kHz, from about 40 kHz to about 100 kHz, from about 50 kHz to about 100 kHz, from about 60 kHz to about 100 kHz, from about 70 kHz to about 100 kHz, from about 80 kHz to about 100 kHz, or from about 90 kHz to about 100 kHz. In yet another embodiment, the coaxial electrodes may be configured to emit and receive an RF signal at a frequency of from about 5 kHz to about 10 kHz, from about 5 kHz to about 20 kHz, from about 5 kHz to about 30 kHz, from about 5 kHz to about 40 kHz, from about 5 kHz to about 50 kHz, from about 5 kHz to about 60 kHz, from about 5 kHz to about 70 kHz, from about 5 kHz to about 80 kHz, or from about 5 kHz to about 90 kHz. In a further embodiment, the coaxial electrodes may be configured to emit and receive an RF signal at a frequency less than 100 kHz, less than 90 kHz, less than 80 kHz, less than 70 kHz, less than 60 kHz, less than 50 kHz, less than 40 kHz, less than 30 kHz, less than 20 kHz, less than 10 kHz, or less than 5 kHz. In certain embodiments, all of the coaxial electrodes of the apparatus may operate at the same frequency. In some embodiments, some of the coaxial electrodes of the apparatus may operate at different frequencies. In certain embodiments, the frequency of a coaxial electrode may be changed through programming specific pins on an integrated circuit in which they are connected.

Figure 3A:
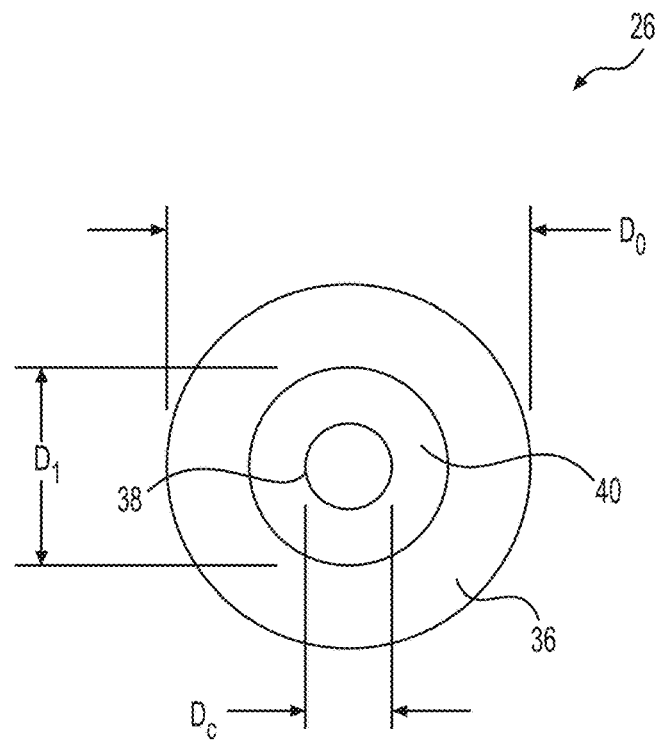
FIG. 3A—An exemplary coaxial electrode according to the present disclosure.

In some embodiments according to the present disclosure, the coaxial electrodes may comprise a bipolar configuration having a first electrode comprising an outer annular ring disposed around a second inner circular electrode. Referring to FIG. 3A, the outer ring electrode may have an outer diameter Do and an inner diameter Di that is larger than the diameter D, of the circular inner electrode. Each inner circular electrode and outer electrode may be coupled electrically to one or more circuits that are capable of applying a voltage waveform to each electrode; generating a bio-impedance signal; and converting the capacitance signal to a SEM value. In certain embodiments, the bioimpedance signal may be a capacitance signal generated by, e.g., measuring the difference of the current waveform applied between the central electrode and the annular ring electrode. In some embodiments, the conversion may be performed by a 24 bit capacitance-to-digital converter. In another embodiment, the conversion may be a 16 bit capacitance-to-digital converter, a charge-timing capacitance to digital converter, a sigma-delta capacitance to digital converter. The one or more circuits may be electronically coupled to a processor. The processor may be configured to receive the SEM value generated by the circuit.

In certain embodiments, the one or more coaxial electrodes may have the same size. In other embodiments, the one or more coaxial electrodes may have different sizes, which may be configured to interrogate the patient's skin at different depths. The dimensions of the one or more coaxial electrodes may correspond to the depth of interrogation into the derma of the patient. Accordingly, a larger diameter electrode may penetrate deeper into the skin than a smaller pad. The desired depth may vary depending on the region of the body being scanned, or the age, skin anatomy or other characteristic of the patient. In some embodiments, the one or more coaxial electrodes may be coupled to two or more separate circuits to allow independent operation of each of the coaxial electrodes. In another embodiment, all, or a subset, of the one or more coaxial electrodes may be coupled to the same circuit.

In some embodiments, the one or more coaxial electrodes may be capable of emitting RF energy to a skin depth of 4 millimeters (mm), 3.5 mm, 3.0 mm, 2.5 mm, 2.0 mm, 1.0 mm, or 0.5 mm. In a further embodiment, the one or more coaxial electrodes may have an outer diameter Do from about 5 mm to about 55 mm, from about 10 mm to about 50 mm, from about 15 mm to about 45 mm, or from about 20 mm to about 40 mm. In another embodiment, the outer ring of the one or more coaxial electrodes may have an inner diameter Di from about 4 mm to about 40 mm, from about 9 mm to about 30 mm, or from about 14 mm to about 25 mm. In yet another embodiment, the inner electrode of the one or more coaxial electrodes may have a diameter Dc from about 2 mm to 7 mm, 3 mm to 6 mm, or 4 mm to 5 mm.

In a further embodiment, the one or more coaxial electrodes may be spaced apart at a distance to avoid interference between the electrodes. The distance may be a function of sensor size and frequency to be applied. In some embodiments, each of the one or more coaxial electrodes may be activated sequentially. In certain embodiments, multiple coaxial electrodes may be activated at the same time.

Figure 3B:
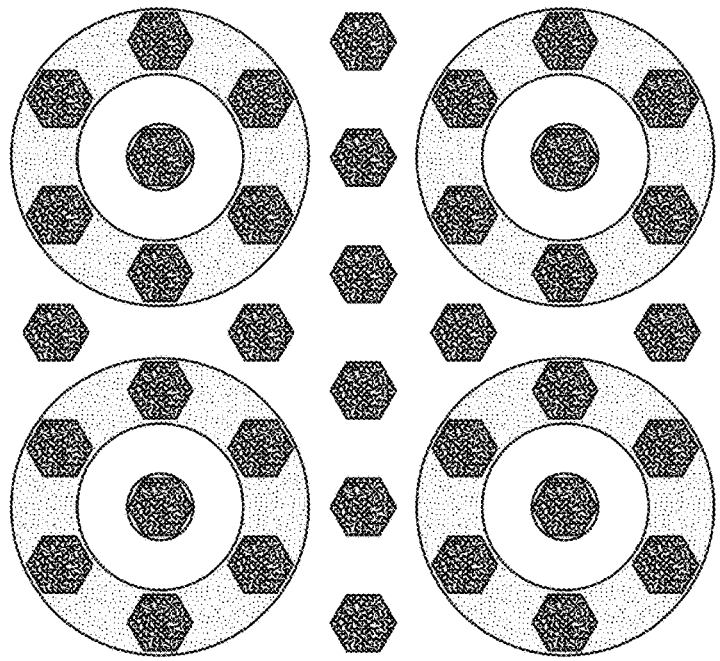
FIG. 3B—Exemplary coaxial electrodes constructed with a point source electrode surrounded by six hexagon pad electrodes according to the present disclosure.
Figure 3C:
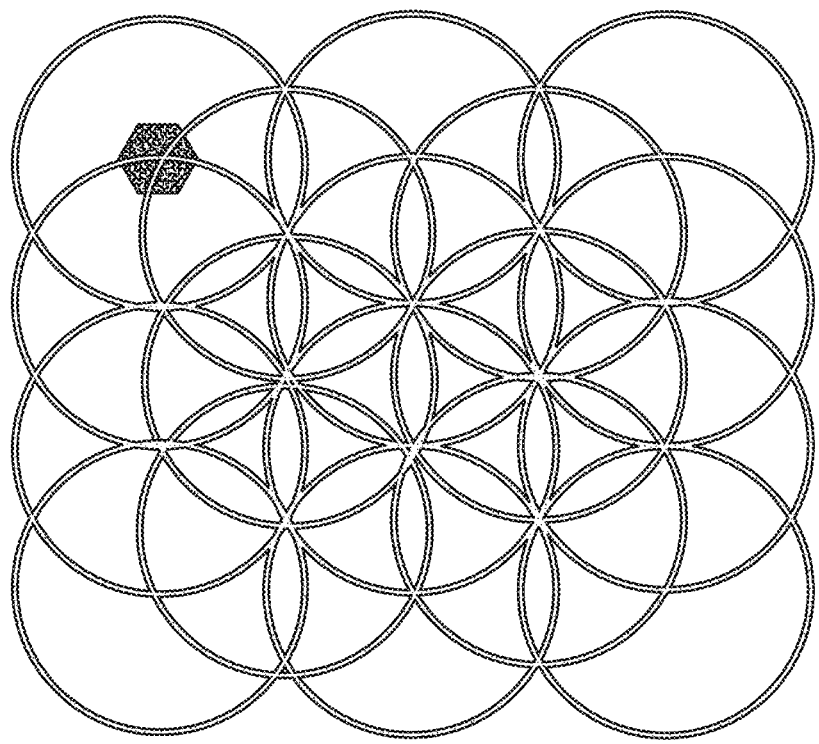
FIG. 3C—An exemplary array of hexagon pad electrodes where each of the electrodes may be programmed to function as different parts of a coaxial electrode in accordance with the present disclosure.
Figure 3D:
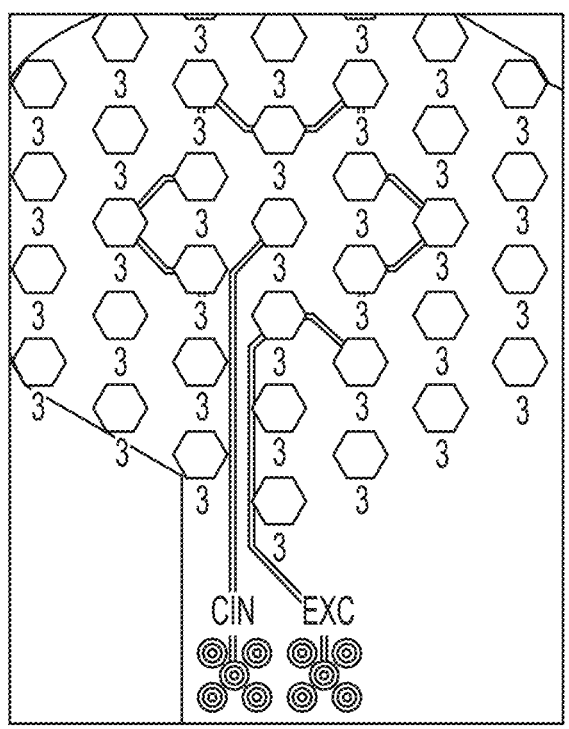
FIG. 3D—Sample electronic connection of an array of hexagonal pad electrodes allowing for coaxial electrode emulation in accordance with the present disclosure.
Figure 3E:
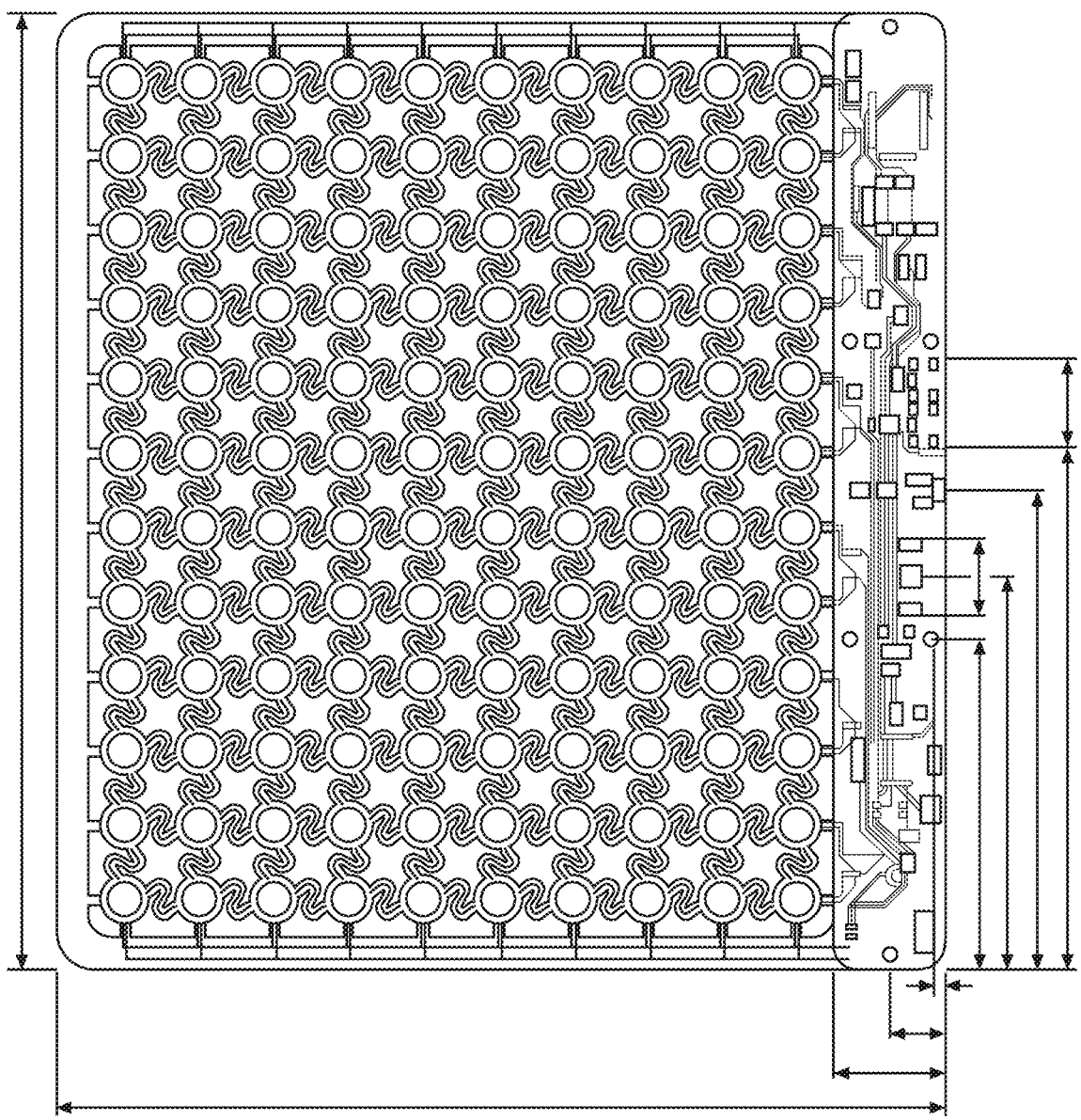
FIG. 3E—An exemplary array of coaxial electrodes electronically coupled together.

In certain embodiments according to the present disclosure, a coaxial electrode may comprise a point source surrounded by hexagon pad electrodes spaced at approximately equidistance, as illustrated in FIG. 3B. The point source may comprise a hexagon pad electrode. In some embodiments, the point source may comprise two, three, four, five, or six hexagon pad electrodes. In certain embodiments, a point source may be surrounded by six hexagon pad electrodes. In some embodiments, multiple coaxial electrodes may be emulated from an array comprising a plurality of hexagon pad electrodes, where each hexagon pad electrode may be programmed to be electronically coupled to a floating ground, a capacitance input, or a capacitance excitation signal, as illustrated in FIGS. 3C and 3D. In a further embodiment, each of the hexagon pad electrodes may be connected to a multiplexer that may have a select line that controls whether the hexagon pad electrode is connected to a capacitance input or a capacitance excitation signal. The multiplexer may also have an enable line that controls whether to connect the hexagon pad electrode to a floating ground. In certain embodiments, the multiplexer may be a pass-gate multiplexer. In some embodiments, the one or more coaxial electrodes may be arranged as illustrated in FIG. 3E to leverage multiplexer technology. Without being limited to theory, the arrangement illustrated in FIG. 3E may limit interference between the one or more coaxial electrodes.

In certain embodiments, one or more coaxial electrodes may be embedded on a first side of a non-conductive substrate. In some embodiments, the substrate may be flexible or hard. In certain embodiments, the flexible substrate may comprise kapton, polyimide, or a combination thereof. In further embodiments, an upper coverlay may be positioned directly above the one or more coaxial electrodes. In certain embodiments, the upper coverlay may be a double-sided, copper-clad laminate and an all-polyimide composite of a polyimide film bonded to copper foil. In some embodiments, the upper coverlay may comprise Pyralux 5 mil FR0150. Without being limited by theory, the use this upper coverlay may avoid parasitic charges naturally present on the skin surface from interfering with the accuracy and precision of SEM measurements. In some embodiments, the one or more coaxial electrodes may be spring mounted to a substrate within an apparatus according to the present disclosure.

In some embodiments, the apparatus may comprise a non-transitory computer readable medium electronically coupled to the processor. In certain embodiments, the non-transitory computer readable medium may comprise instructions stored thereon that, when executed on a processor, may perform the steps of: (1) receiving at least one SEM value at an anatomical site; (2) receiving at least two SEM values measured around the anatomical site and their relative measurement locations; (3) determining a maximum SEM value from the measurements around the anatomical site; (4) determining a difference between the maximum SEM value and each of the at least two SEM values measured around the anatomical site; and (5) flagging the relative measurement locations associated with a difference greater than a predetermined value as damaged tissue. In another embodiment, the non-transitory computer readable medium may comprise instructions stored thereon that may carry out the following steps when executed by the processor: (1) receiving at least one SEM value measured at an anatomical site; (2) receiving at least two SEM values measured around the anatomical site, and their relative measurement locations; (3) determining an average SEM value for each group of SEM values measured at approximately equidistance from the anatomical site; (4) determining a maximum SEM value from the average SEM values; (5) determining a difference between the maximum average SEM value and each of the average SEM values measured around the anatomical site; and (6) flagging the relative measurement locations associated with a difference greater than a predetermined value as damaged tissue. In yet another embodiment, the non-transitory computer readable medium may comprise instructions stored thereon that, when executed on a processor, may perform the steps of: (1) receiving at least one SEM value at an anatomical site; (2) receiving at least two SEM values measured around the anatomical site and their relative measurement locations; (3) determining a maximum SEM value from the measurements around the anatomical site; (4) determining a minimum SEM value from the measurements around the anatomical site; (5) determining a difference between the maximum SEM value and the minimum SEM value; and (6) flagging the relative measurement locations associated with a difference greater than a predetermined value as damaged tissue. In some embodiments, the predetermined value may be 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. It will be understood that the predetermined value is not limited by design, but rather, one of ordinary skill in the art would be capable of choosing a predetermined value based on a given unit of SEM.

In further embodiments, the leading edge of inflammation may be indicated by an SEM difference that is equal to or greater than the predetermined value. In some embodiments, the leading edge of inflammation may be identified by the maximum values out of a set of SEM measurements.

In certain embodiments, an anatomical site may be a bony prominence. In further embodiments, an anatomical site may be a sternum, sacrum, a heel, a scapula, an elbow, an ear, or other fleshy tissue. In some embodiments, one SEM value is measured at the anatomical site. In another embodiment, an average SEM value at the anatomical site is obtained from two, three, four, five, six, seven, eight, nine, ten, or more than ten SEM values measured at the anatomical site.

The apparatuses of the present disclosure may allow the user to control the pressure applied onto a patient's skin to allow for optimized measurement conditions. In certain embodiments, a first pressure sensor may be placed on a second side opposing the first side of the substrate that the coaxial electrodes are disposed on. In a further embodiment, a second pressure sensor may be disposed on a second side opposing the first side of the substrate that the coaxial electrodes are disposed on. In certain embodiments, the first pressure sensor may be a low pressure sensor, and the second pressure sensor may be a high pressure sensor. Together, the first and second pressure sensors may allow measurements to be taken at a predetermined range of target pressures. In some embodiments, a target pressure may be about 500 g. It will be understood that the high and low pressure sensors are not limited by design, but rather, one of ordinary skill in the art would be capable of choosing these sensors based on a given range of target pressures. The first and second pressure sensors may be resistive pressure sensors. In some embodiments, the first and second pressure sensors may be sandwiched between the substrate and a conformal pressure pad. The conformal pressure pad may provide both support and conformity to enable measurements over body curvature and bony prominences.

In an embodiment, the apparatus may further comprise a plurality of contact sensors on the same planar surface as, and surrounding, each of the one or more coaxial electrodes to ensure complete contact of the one or more coaxial electrodes to the skin surface. The plurality of contact sensors may be a plurality of pressure sensors, a plurality of light sensors, a plurality of temperature sensors, a plurality of pH sensors, a plurality of perspiration sensors, a plurality of ultrasonic sensors, a plurality of bone growth stimulator sensors, or a plurality of a combination of these sensors. In some embodiments, the plurality of contact sensors may comprise four, five, six, seven, eight, nine, or ten or more contact sensors surrounding the one or more coaxial electrodes.

In certain embodiments, the apparatus may comprise a temperature probe. In some embodiments, the temperature probe may be a thermocouple or an infrared thermometer.

In some embodiments, the apparatus may further comprise a display having a user interface. The user interface may allow the user to input measurement location data. The user interface may further allow the user to view measured SEM values and/or damaged tissue locations. In certain embodiments, the apparatus may further comprise a transceiver circuit configured to receive data from and transmit data to a remote device, such as a computer, tablet or other mobile or wearable device. The transceiver circuit may allow for any suitable form of wired or wireless data transmission such as, for example, USB, Bluetooth, or Wifi.

Figure 4:
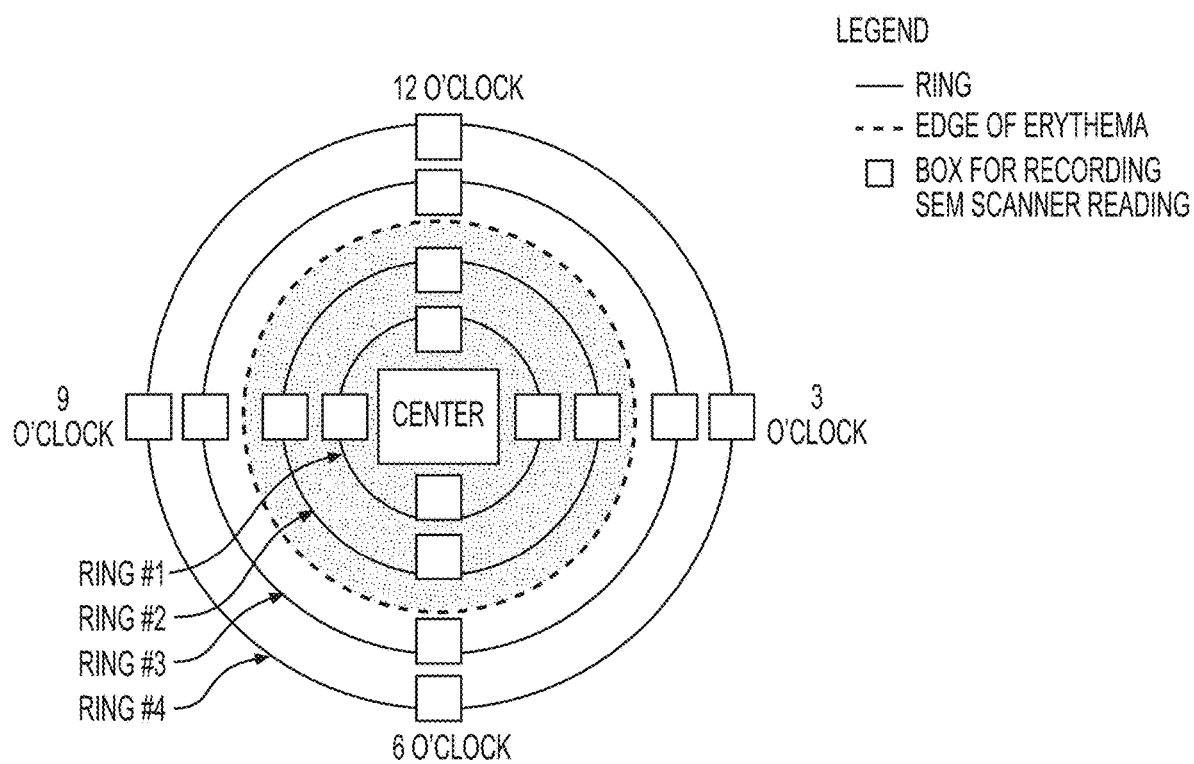
FIG. 4—A sample measurement scheme according to the present disclosure.

Methods according to the present disclosure provide for identifying damaged tissue. In some embodiments, the method may comprise measuring at least three SEM values at and around an anatomical site using an apparatus of the present invention, and obtaining from the apparatus measurement locations that are flagged as damaged tissue. In certain embodiments, measurements may be taken at positions that are located on one or more concentric circles about an anatomic site. FIG. 4 provides a sample measurement strategy, with the center being defined by an anatomic site. In another embodiments, the measurements may be taken spatially apart from an anatomic site. In yet another embodiment, the measurements may be taken on a straight line across an anatomic site. In a further embodiment, the measurements may be taken on a curve around an anatomic site. In certain embodiment, surface moisture and matter above a patient's skin surface may be removed prior to the measuring step. In some embodiments, the measuring step may take less than one second, less than two seconds, less than three seconds, less than four seconds, or less than five seconds.

Having now generally described the invention, the same will be more readily understood through reference to the following examples that are provided by way of illustration, and are not intended to be limiting of the present disclosure, unless specified.

EXAMPLES

Example 1: Measuring Sub-Epidermal Moisture (SEM) Values at the Bony Prominence of the Sacrum Subjects with visually-confirmed Stage I or II pressure ulcers with unbroken skin were subjected to multiple SEM measurements at and around the boney prominence of the sacrum using an apparatus of this disclosure. Prior to performing the measurements, surface moisture and matter above the subjects' skin surface were removed. An electrode of the apparatus was applied to the desired anatomical site with sufficient pressure to ensure complete contact for approximately one second. Additional measurements were taken at the mapped location as laid out in FIG. 4.

Figure 5A:
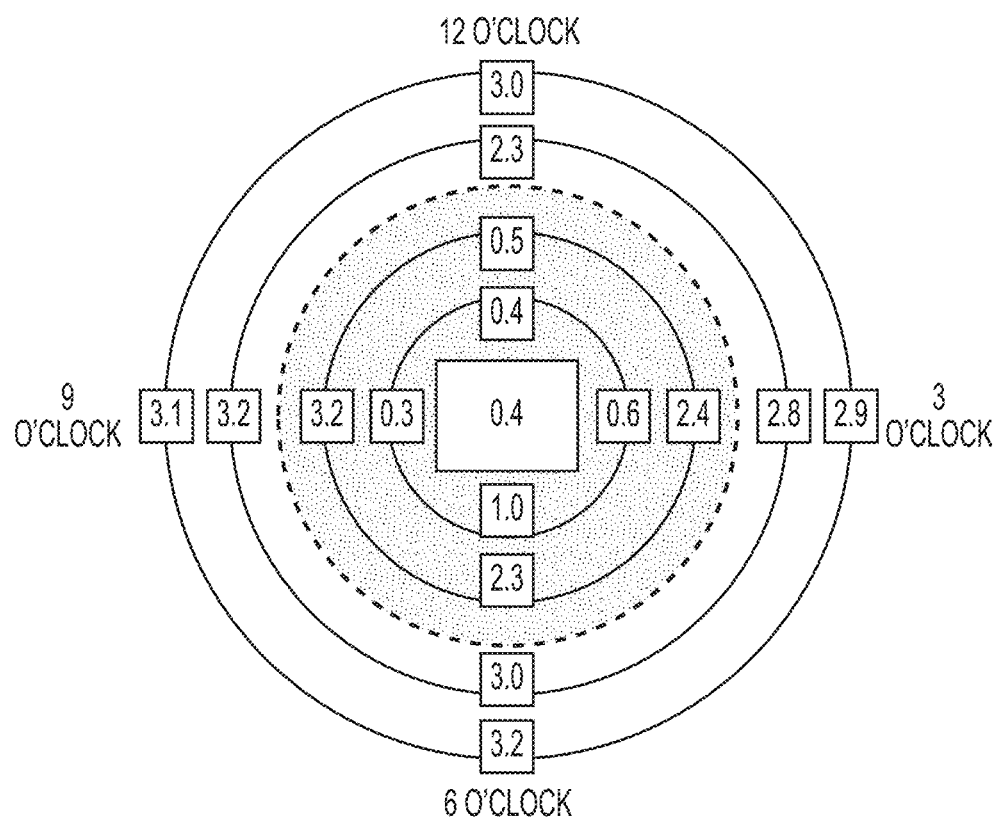
FIG. 5A—Sample SEM measurement results obtained in accordance with the methods in the present disclosure, represented as a SEM map.
Figure 5B:
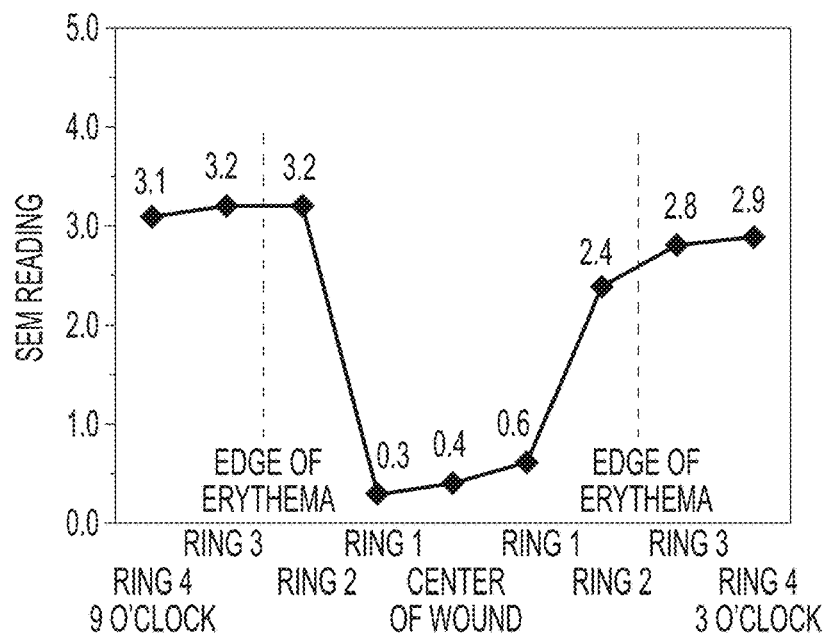
FIG. 5B—Sample SEM measurement results along the x-axis of FIG. 5A plotted on a graph.
Figure 5C:
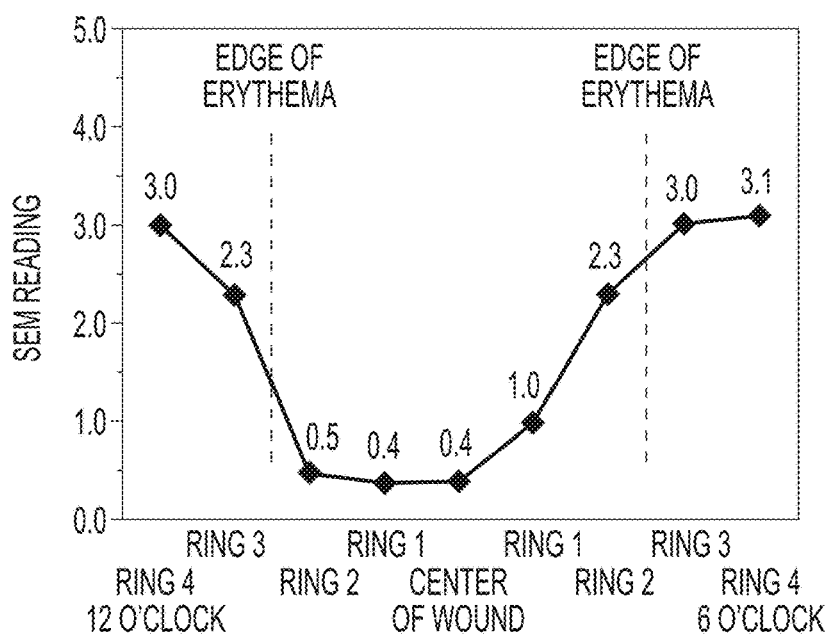
FIG. 5C—Sample SEM measurement results along the y-axis of FIG. 5A plotted on a graph.

FIG. 5A shows a sample SEM map centered on an anatomical site. FIG. 5B is a plot of the individual SEM values across the x-axis of the SEM map. FIG. 5C is a plot of the individual SEM values across the y-axis of the SEM map. Damaged tissue radiated from the center anatomical site to an edge of erythema defined by a difference in SEM values of greater than 0.5.

Example 2: Taking SEM Measurements at the Bony Prominence of the Heel

SEM measurements were taken at the heel using one of three methods below to ensure complete contact of an electrode with the skin of a human patient.

Figure 6A:
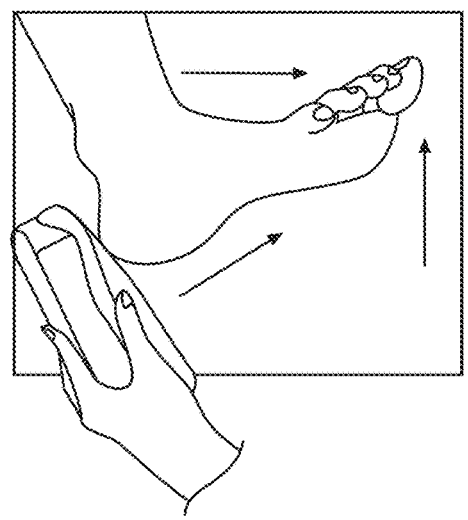
FIG. 6A—An exemplary method for taking SEM measurements starting at the posterior heel.

FIG. 6A illustrates a method used to take SEM measurements starting at the posterior heel using an apparatus according to the present disclosure. First, the forefoot was dorsiflexed such that the toes were pointing towards the shin. Second, an electrode was positioned at the base of the heel. The electrode was adjusted for full contact with the heel, and multiple SEM measurements were then taken in a straight line towards the toes.

Figure 6B:
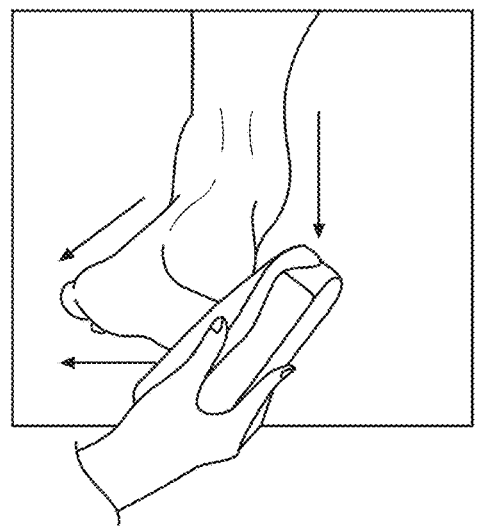
FIG. 6B—An exemplary method for taking SEM measurements starting at the lateral heel.

FIG. 6B illustrates a method used to take SEM measurements starting at the lateral heel using an apparatus according to the present disclosure. First, the toes were pointed away from the body and rotated inward towards the medial side of the body. Second, an electrode was placed on the lateral side of the heel. The electrode was adjusted for full contact with the heel, and multiple SEM measurements were taken in a straight line towards the bottom of the foot.

Figure 6C:
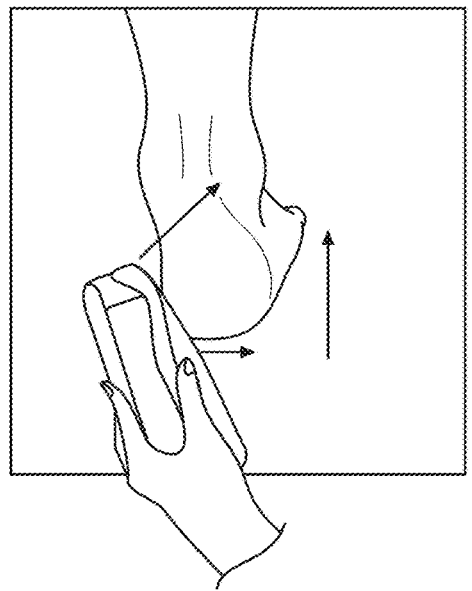
FIG. 6C—An exemplary method for taking SEM measurements starting at the medial heel.

FIG. 6C illustrates a method used to take SEM measurements starting at the medial heel using an apparatus according to the present disclosure. First, the toes were pointed away from the body and rotated outwards toward the lateral side of the body. Second, the electrode was placed on the medial side of the heel. The electrode was adjusted for full contact with the heel, and multiple measurements were taken around the back of the heel in a curve.

Example 3: Identifying a Region of Damaged Tissue

Figure 7A:
FIG. 7A—Sample visual assessment of damaged tissue around a sacrum.
Figure 7B:
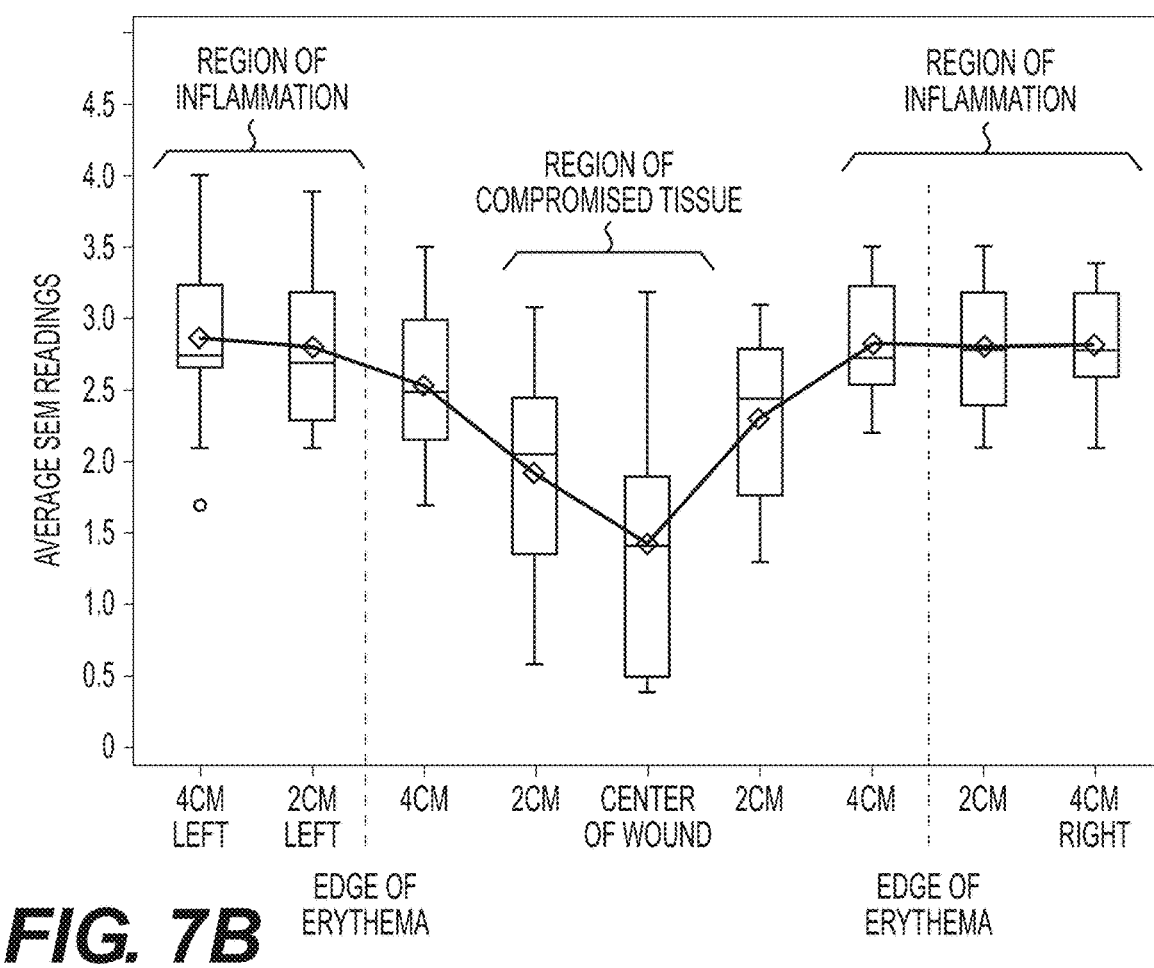
FIG. 7B—Sample SEM measurement results of damaged tissue obtained in accordance with the methods in the present disclosure.

SEM measurements were taken on a straight line, each spaced apart by 2 cm, across the sacrum of a patient. Multiple measurements were taken at a given measurement location. FIG. 7A is a sample visual assessment of damaged tissue. FIG. 7B is a corresponding plot of the averages of SEM measurements taken at each location. The edges of erythema are defined by differences in SEM values of greater than 0.5.

Example 4: SEM Measurements of Healthy Tissue

Figure 8A:
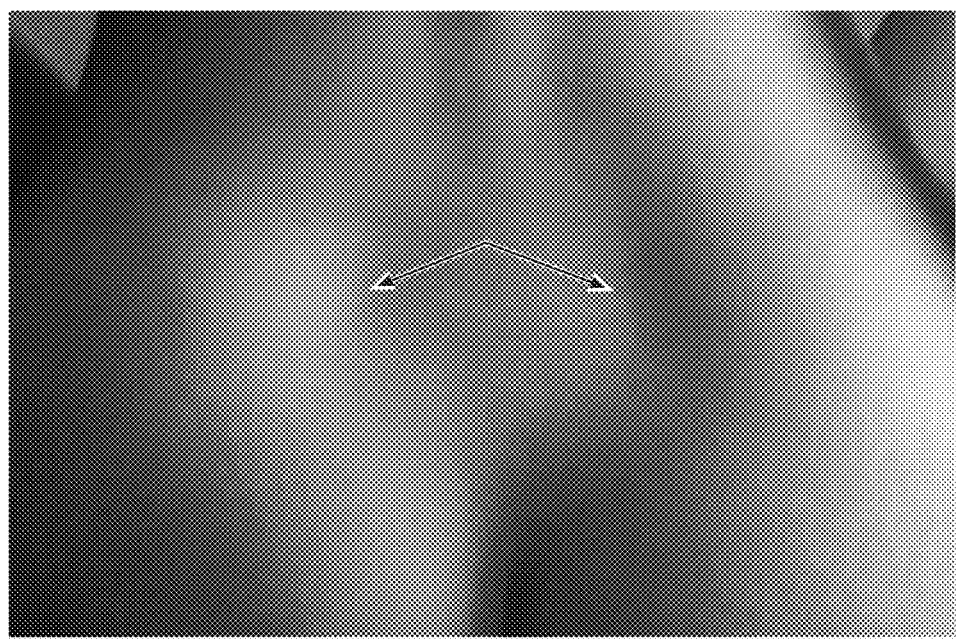
FIG. 8A—Sample visual assessment of healthy tissue around a sacrum.
Figure 8B:
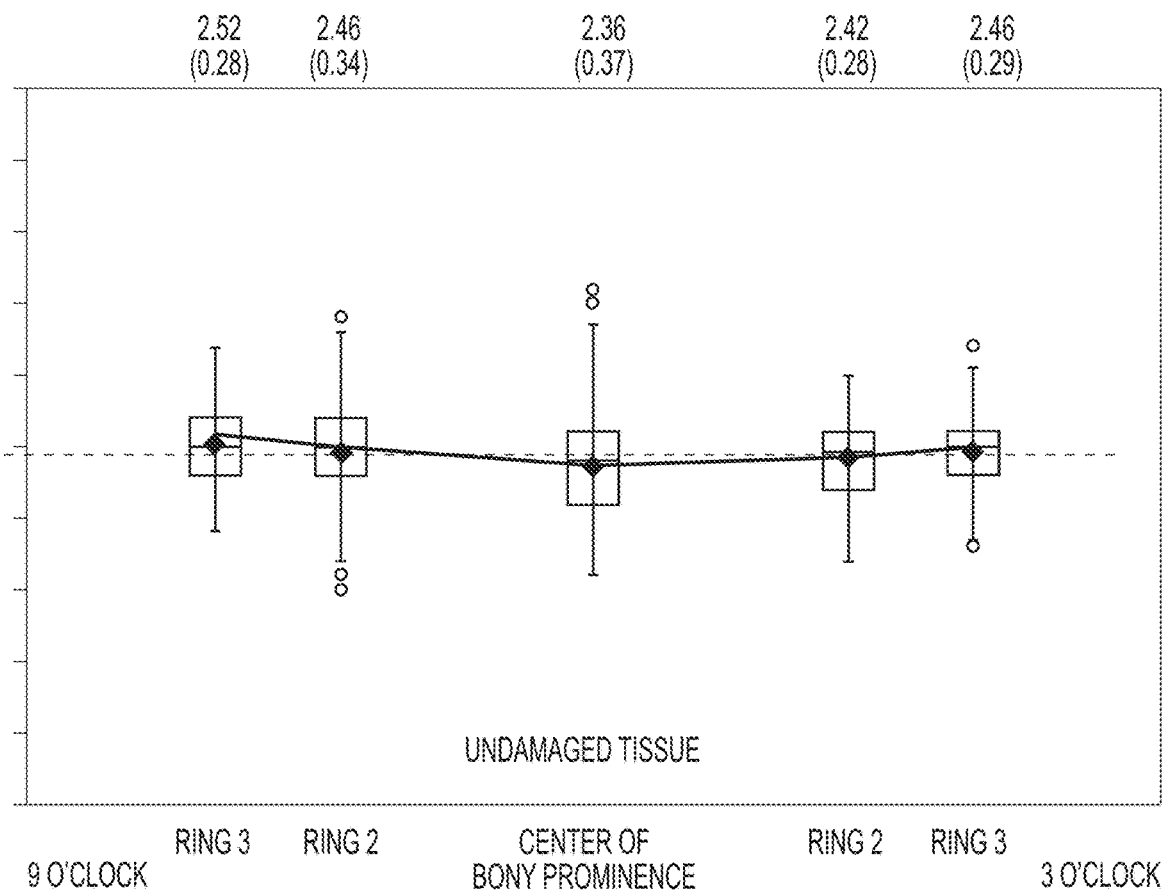
FIG. 8B—Sample SEM measurement results of healthy tissue obtained in accordance with the methods in the present disclosure.

SEM measurements were taken on a straight line across the sacrum of a patient. Multiple measurements were taken at a given measurement location. FIG. 8A is a sample visual assessment of healthy tissue. FIG. 8B is a corresponding plot of the averages of SEM measurements taken at each location. The tissue is defined as healthy as the differences in SEM values are all less than 0.5.

Example 5: SEM Measurement Map of Damaged Tissue

Figure 9B:
FIG. 9B—Corresponding visual assessment of damaged tissue of FIG. 9A.
Figure 9A:
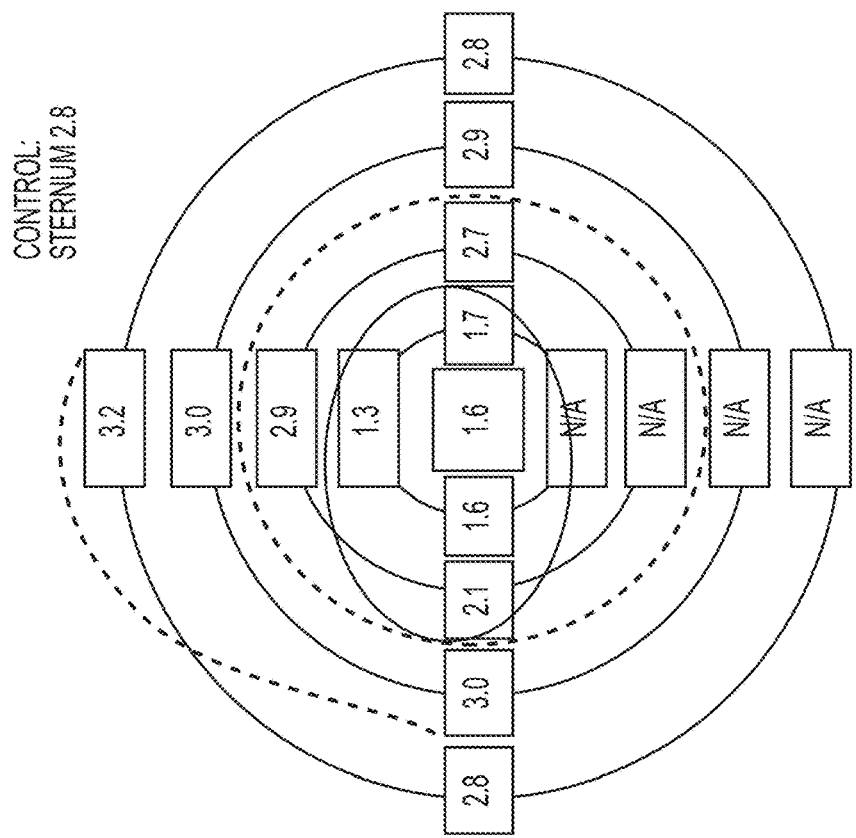
FIG. 9A—A sample SEM map obtained in accordance with the methods in the present disclosure.

SEM measurements were taken in accordance with Example 1. FIG. 9A is a sample map of averaged SEM values taken on concentric rings around an anatomical site. FIG. 9B is the corresponding visual assessment of the patient's skin. Compromised tissue is identified by the solid circle, where the difference in SEM values compared to the maximum SEM value is greater than 0.5. The leading edge of inflammation is identified by the dotted circle, where the difference in SEM values compared to the maximum SEM value is equal to or greater than 0.5. The leading edge of inflammation is identified by a dotted line, indicating the largest values in the SEM map.

Example 6: Sample SEM Measurement Image Representations

Figure 10:
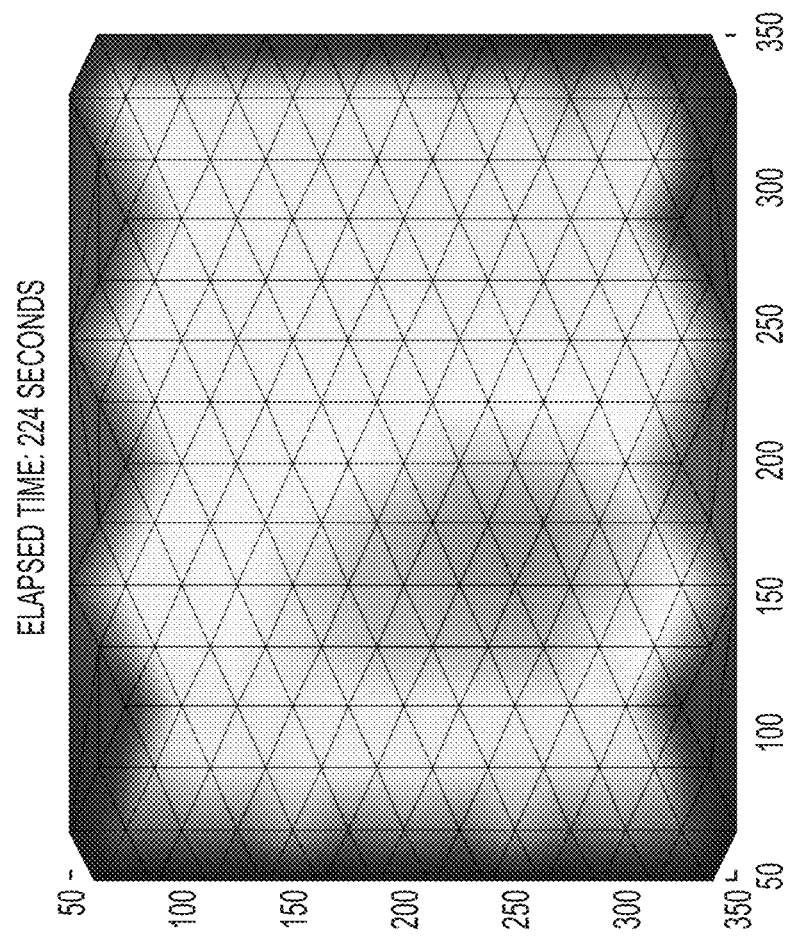
FIG. 10—A sample SEM image obtained in accordance with the methods in the present disclosure.

SEM measurements were taken with an array of coaxial electrodes. FIG. 10 is a sample output of a SEM measurement image showing the moisture content of the skin over a defined area. Different SEM values are indicated by different colors.

Example 7: SEM Measurements of Skin Moisture Content Over Time

Figure 11:
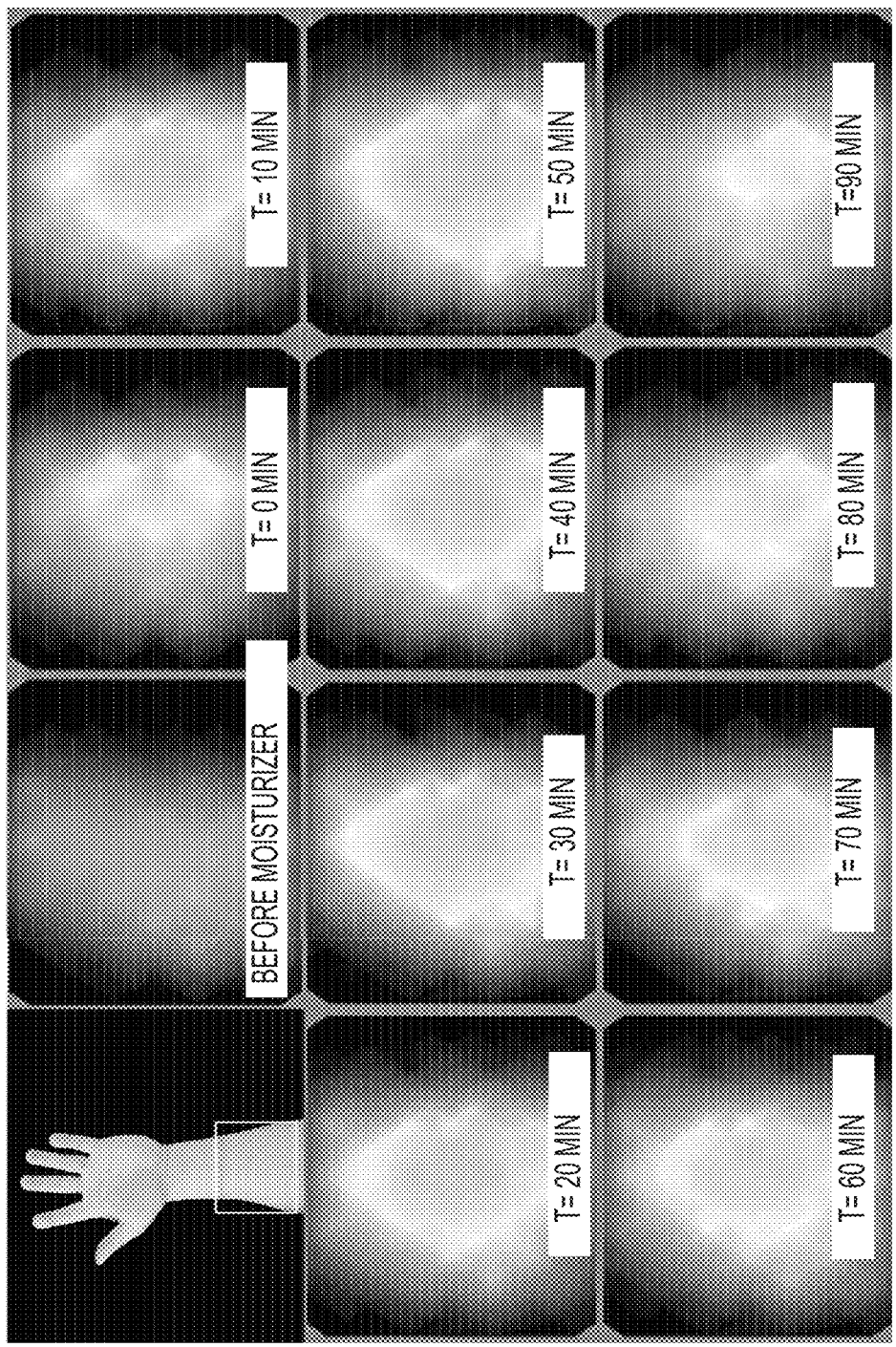
FIG. 11—Sample time-lapsed SEM images showing the sensitivity of the detection apparatuses and methods in the present disclosure.

Moisturizer was used to simulate the onset of a pressure ulcer. 0.2 mL moisturizer was applied to the inner forearm of a subject for 60 seconds. The moisturizer was then wiped from the skin. SEM measurements were taken with an array of coaxial electrodes every 10 minutes for 2 hours. FIG. 11 shows a sample time lapse of an SEM measurement image to monitor moisture content of a test subject.

Example 8: Selecting an Optimal Electrode for Interrogating Patient Skin

FIG. 12A is a sample graphical representation of a finite element model showing the depth of various SEM levels in accordance with the methods in the present disclosure. Each line indicates a SEM value and the depth of the moisture content.

Actual SEM levels in various depths of a skin-like material were measured using an apparatus according to the present disclosure. Specifically, the apparatus comprises one coaxial electrode. First, the thickness of a blister bandage, which simulates a skin-like material, was measured and placed on the coaxial electrode. A downward force was then applied via a metal onto the coaxial electrode, in an acceptable range according to the present disclosure. The metal is fitted to a second metal in tubular form. The second metal was selected from brass, aluminum, and stainless steel. The SEM measurement was recorded. Additional blister bandages were placed atop the coaxial electrodes for further SEM measurement recordings. FIG. 12B is a sample plot of SEM measurements at various thicknesses of the blister bandages. Without being limited by theory, the variations in the SEM values in the presence of different tubular metal may be due to potential magnetic field interference. The maximum depth of a magnetic field generated by the coaxial sensor was determined by the distance from the coaxial sensor when the metal tube no longer interfered with the magnetic field. In this example, the maximum depth ranged from 0.135 inches to 0.145 inches. Accordingly, electrodes having an optimal penetration depth could be selected to interrogate specific depths of patient skin.

While the invention has been described with reference to particular embodiments, it will be understood by those skilled in the art that various changes may be made and equivalents may be substituted for elements thereof without departing from the scope of the invention. In addition, many modifications may be made to a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

The invention claimed is:

1. An apparatus for identifying sub-epidermal moisture (SEM), said apparatus comprising:
   a) one or more sensors configured for emitting and receiving (i) a target signal into tissue at a target location of a subject and (ii) a plurality of non-target signals into non-target tissue locations adjacent to said target location of said subject, b) a circuit electronically coupled to said one or more sensors and configured to convert said target signal into a target SEM value and said plurality of non-target signals into a plurality of non-target SEM values;

c) a processor electronically coupled to said circuit and configured to receive said target SEM value and said plurality of non-target SEM values; and d) a non-transitory computer readable medium electronically coupled to said processor and comprising instructions stored thereon that when executed on said processor, perform:
  i) receiving from said processor said target SEM value, said plurality of non-target SEM values, said target location, and said non-target tissue locations;
  ii) determining a) a maximum SEM value and a minimum SEM value from said plurality of non-target SEM values and said target SEM value or b) an average SEM value from said plurality of non-target SEM values and said target SEM value;
  iii) determining a difference between a) said maximum SEM value and said minimum SEM value or b) said average SEM value and at least one of said plurality of non-target SEM values or said target SEM value; and
  iv) identifying said target location or said non-target locations as having a SEM indicative of tissue damage if said difference is greater than a predetermined threshold.

2. The apparatus of claim 1, further comprising a substrate, wherein said one or more sensors are embedded on a first side of said substrate.

3. The apparatus of claim 1, wherein said one or more sensors are configured to conform to a non-planar sensing surface of said subject's skin.

4. The apparatus of claim 1, wherein said non-target tissue locations are equidistant from said target location.

5. The apparatus of claim 1, wherein said non-target tissue locations are spaced apart equally from one another.

6. The apparatus of claim 1, wherein identifying comprises plotting said target SEM value and said plurality of non-target SEM values on a graphical representation of said target location.

7. The apparatus of claim 1, wherein said target signal and said plurality of non-target signals are received from a target depth within said tissue.

8. The apparatus of claim 7, wherein said one or more sensors are selected to emit said target signal and said plurality of non-target signals to said target depth.

9. The apparatus of claim 8, wherein said target depth is selected based on said target location, an age of said subject, or a skin anatomy of said subject.

10. The apparatus of claim 7, wherein said target depth is at least 0.5 millimeters.

11. The apparatus of claim 7, wherein said target depth is at least 4 millimeters.

12. The apparatus of claim 1, wherein said plurality of non-target tissue locations are on one or more concentric circles around said target location.

13. The apparatus of claim 1, wherein i) through iv) are repeated over a period of time.

14. The apparatus of claim 1, wherein a shape of said one or more sensors comprise a ring coaxial to at least one sensor.

15. The apparatus of claim 1, wherein said one or more sensors have a substantially round or elliptic shape.

16. A method comprising:
a) emitting a plurality of first signals into a subject's skin at a target location of said subject's skin and one or more non-target locations adjacent to said target location of said subject's skin;
b) receiving a plurality of second signals derived from said first signals from said subject's skin at said target location and said one or more non-target locations;
c) converting said plurality of second signals into a target sub-epidermal moisture (SEM) value and a plurality of non-target SEM values;
d) determining i) a maximum SEM value and a minimum SEM value from said plurality of non-target SEM values and said target SEM value or ii) an average SEM value from said plurality of non-target SEM values and said target SEM value;
e) determining a difference between i) said maximum SEM value and said minimum SEM value or ii) said average SEM value and at least one of said plurality of non-target SEM values or said target SEM value; and
f) identifying said target location or said one or more non-target locations as having a SEM indicative of tissue damage if said difference is greater than a predetermined threshold.

17. The method of claim 16, wherein a) through f) are repeated over a period of time.

18. The method of claim 16, wherein a) and b) are performed using one or more sensors.

19. The method of claim 18, wherein said one or more sensors are embedded on a first side of a substrate.

20. The method of claim 19, wherein said substrate is flexible.

21. The method of claim 19, wherein said substrate is rigid.

22. The method of claim 18, wherein said one or more sensors are configured to conform to a non-planar sensing surface of said subject's skin.

23. The method of claim 22, wherein said non-planar sensing surface comprises a body curvature or bony prominence.

24. The method of claim 23, wherein said bony prominence is a heel, a sternum, sacrum, a scapula, an elbow, or an ear of said subject.

25. The method of claim 16, further comprising plotting said target SEM value and said plurality of non-target SEM values on a graphical representation of said target location.

26. The method of claim 16, wherein said one or more non-target locations are equidistant from said target location.

27. The method of claim 16, wherein said one or more non-target locations are spaced apart equally from one another.

28. The method of claim 18, wherein said plurality of second signals are received from a target depth within said tissue.

29. The method of claim 28, further comprising, before a), selecting said one or more sensors to emit said plurality of first signals to said target depth.

30. The method of claim 29, further comprising selecting said target depth based on said target location, an age of said subject, or a skin anatomy of said subject.

* * * * *